US009737536B2

(12) United States Patent
Giblin et al.

(10) Patent No.: US 9,737,536 B2
(45) Date of Patent: *Aug. 22, 2017

(54) PYRIMIDINYL-DIAZOSPIRO COMPOUNDS

(71) Applicant: CONVERGENCE PHARMACEUTICALS LIMITED, London (GB)

(72) Inventors: Gerard M. P. Giblin, Cambridge (GB); David T. MacPherson, Cambridge (GB); David R. Witty, Cambridge (GB); Steven J. Stanway, Cambridge (GB)

(73) Assignee: Convergence Pharmaceuticals Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/163,845

(22) Filed: May 25, 2016

(65) Prior Publication Data

US 2016/0263115 A1    Sep. 15, 2016

Related U.S. Application Data

(63) Continuation of application No. 14/403,473, filed as application No. PCT/GB2013/051335 on May 22, 2013, now Pat. No. 9,376,445.

(60) Provisional application No. 61/773,710, filed on Mar. 6, 2013, provisional application No. 61/650,325, filed on May 22, 2012.

(30) Foreign Application Priority Data

May 22, 2012 (GB) .................................. 1209015.5

(51) Int. Cl.
| | |
|---|---|
| *C07D 471/10* | (2006.01) |
| *C07D 487/10* | (2006.01) |
| *A61K 31/407* | (2006.01) |
| *A61K 31/506* | (2006.01) |
| *A61K 31/438* | (2006.01) |

(52) U.S. Cl.
CPC .......... *A61K 31/506* (2013.01); *A61K 31/407* (2013.01); *A61K 31/438* (2013.01); *C07D 471/10* (2013.01); *C07D 487/10* (2013.01)

(58) Field of Classification Search
CPC .. C07D 471/10; C07D 487/10; A61K 31/407; A61K 31/438
USPC .......................... 544/242, 333, 335; 514/256
See application file for complete search history.

(56) References Cited

U.S. PATENT DOCUMENTS

| | | | |
|---|---|---|---|
| 7,655,693 B2 | 2/2010 | Alvaro et al. | |
| 7,803,833 B2 | 9/2010 | Alvaro et al. | |
| 7,855,218 B2 | 12/2010 | Alvaro et al. | |
| 8,093,268 B2 | 1/2012 | Alvaro et al. | |
| 8,143,306 B2 | 3/2012 | Alvaro et al. | |
| 8,153,623 B2 | 4/2012 | Alvaro et al. | |
| 8,153,681 B2 | 4/2012 | Alvaro et al. | |
| 8,759,542 B2 | 6/2014 | Zajac | |
| 9,309,254 B2* | 4/2016 | Giblin ................. | C07D 487/10 |
| 9,376,445 B2* | 6/2016 | Giblin ................. | C07D 487/10 |
| 2008/0293753 A1 | 11/2008 | Alvaro et al. | |
| 2009/0318530 A1 | 12/2009 | Alvaro et al. | |
| 2009/0326032 A1 | 12/2009 | Alvaro et al. | |
| 2010/0105688 A1 | 4/2010 | Alvaro et al. | |
| 2010/0130583 A1 | 5/2010 | Alvaro et al. | |
| 2014/0350040 A1 | 11/2014 | Witty et al. | |
| 2015/0225400 A1 | 8/2015 | Witty et al. | |

FOREIGN PATENT DOCUMENTS

| | | |
|---|---|---|
| WO | 2007042239 A1 | 4/2007 |
| WO | 2007042240 A1 | 4/2007 |
| WO | 2007042250 A1 | 4/2007 |
| WO | 2008090114 A1 | 7/2008 |
| WO | 2008122546 A1 | 10/2008 |
| WO | 2013093496 A1 | 6/2013 |
| WO | 2013093497 A1 | 6/2013 |
| WO | 2013179049 A1 | 12/2013 |

OTHER PUBLICATIONS

Eijkelkamp, Niels, et al., "Neurological perspectives on voltage-gated sodium channels," Brain: A Journal of Neurology, 135, pp. 2585-2612 (2012).

Large, C.H., et al., "The efficacy of sodium channel blockers to prevent phencyclidine-induced cognitive dysfunction in the rat: potential for novel treatments for schizophrenia," J Pharmacol Exp Ther. Jul. 2011; 338(1):100-13. doi: 10.1124/jpet.110.178475. Epub Apr. 12, 2011; PMID: 21487071 http://www.ncbi.nlm.nih.gov/pubmed/21487071.

Large, C.H., et al., "The relationship between sodium channel inhibition and anticonvulsant activity in a model of generalised seizure in the rat," Epilepsy Res. Jul. 2009: 85(1):96-106. doi: 10.1016/j.eplepsyres.2009.02.018. Epub Mar. 28, 2009. PMID: 19329281 http://www.ncbi.nlm.nih.gov/pubmed/19329281.

* cited by examiner

*Primary Examiner* — Deepak Rao
(74) *Attorney, Agent, or Firm* — Honigman Miller Schwartz and Cohn LLP; Kathryn D. Doyle; Jonahan P. O'Brien

(57) ABSTRACT

The invention relates to spiro derivatives, to the use of said derivatives intreating diseases and conditions mediated by modulation of voltage-gated sodium channels, to compositions containing said derivatives and processes for their preparation.

13 Claims, No Drawings

PYRIMIDINYL-DIAZOSPIRO COMPOUNDS

FIELD OF THE INVENTION

The invention relates to spiro derivatives, to the use of said derivatives in treating diseases and conditions mediated by modulation of voltage-gated sodium channels, to compositions containing said derivatives and processes for their preparation.

BACKGROUND OF THE INVENTION

Voltage-gated sodium channels are responsible for the initial phase of the action potential, which is a wave of electrical depolarisation usually initiated at the soma of the neuron and propagated along the axon to the terminals. At the terminals, the action potential triggers the influx of calcium and the release of neurotransmitter. Drugs, such as lidocaine, that block voltage-gated sodium channels are used as local anaesthetics. Other sodium channel blockers, such as lamotrigine and carbamazepine are used to treat epilepsy. In the latter case, partial inhibition of voltage-gated sodium channels reduces neuronal excitability and reduces seizure propagation. In the case of local anaesthetics, regional block of sodium channels on sensory neurons prevents the conduction of painful stimuli. A key feature of these drugs is their state-dependent mechanism of action. The drugs are thought to stabilise an inactivated conformation of the channel that is adopted rapidly after the channel opens. This inactivated state provides a refractory period before the channel returns to its resting (closed) state ready to be reactivated. As a result, state-dependent sodium channel blockers inhibit the firing of neurons at high frequency, for example in response to painful stimuli, and will help to prevent repetitive firing during periods of prolonged neuronal depolarisation that might occur, for example, during a seizure. Action potentials triggered at lower frequencies, for example in the heart, will not be significantly affected by these drugs, although the safety margin differs in each case, since at high enough concentrations each of these drugs is capable of blocking the resting or open states of the channels.

The voltage-gated sodium channel family is made up of 9 subtypes, four of which are found in the brain, NaV1.1, 1.2, 1.3 and 1.6. Of the other subtypes, NaV1.4 is found only in skeletal muscle, NaV1.5 is specific to cardiac muscle, and NaV1.7, 1.8, and 1.9 are found predominantly in sensory neurons. The hypothesised binding site for state-dependent sodium channel blockers is the local anaesthetic (LA) binding site in the inner vestibule of the pore on transmembrane S6 of domain IV. Critical residues are located in a highly conserved region among the different subtypes, thus presenting a challenge for the design of new subtype selective drugs. Drugs such as lidocaine, lamotrigine and carbamazepine do not distinguish between the subtypes. However, selectivity can be achieved, and can be further enhanced functionally, as a result of the different frequencies at which the channels operate.

Drugs that block voltage-gated sodium channels in a state-dependent manner are also used in the treatment of bipolar disorder, either to reduce symptoms of mania or depression, or as mood stabilisers to prevent the emergence of mood episodes. Clinical and preclinical evidence also suggests that state-dependent sodium channel blockers may help to reduce the symptoms of schizophrenia. For example, lamotrigine has been shown to reduce symptoms of psychosis induced by ketamine in healthy human volunteers, and furthermore, studies in patients suggest that the drug can augment the antipsychotic efficacy of some atypical antipsychotic drugs, such as clozapine or olanzapine. It is hypothesised that efficacy in these psychiatric disorders may result in part from a reduction of excessive glutamate release. The reduction in glutamate release is thought to be a consequence of sodium channel inhibition in key brain areas, such as the frontal cortex. However, interaction with voltage-gated calcium channels may also contribute to the efficacy of these drugs.

WO 2007/042240 (Glaxo Group Limited) describes a series of quaternary alpha-aminocarboxamide derivatives as modulators of voltage-gated sodium channels.

The object of the invention is to identify alternative compounds which modulate voltage-gated sodium channels.

SUMMARY OF THE INVENTION

According to a first aspect, the invention provides a compound of formula (I) which is 7-methyl-2-[4-methyl-6-[4-(trifluoromethyl)-phenyl]pyrimidin-2-yl]-1,7-diazaspiro[4.4]nonan-6-one:

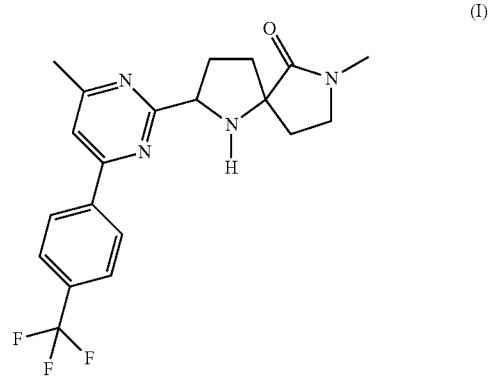 [SMILES: Cc1cc(-c2ccc(C(F)(F)F)cc2)nc(C2CCC3(CCN(C)C3=O)N2)n1]

or a pharmaceutically acceptable salt or solvate thereof.

DETAILED DESCRIPTION OF THE INVENTION

A reference to a compound of the formula (I) and subgroups thereof also includes ionic forms, salts, solvates, isomers (including geometric and stereochemical isomers), tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof. Hereinafter, compounds and their ionic forms, salts, solvates, isomers (including geometric and stereochemical isomers), tautomers, N-oxides, esters, prodrugs, isotopes and protected forms thereof as defined in any aspect of the invention (except intermediate compounds in chemical processes) are referred to as "compounds of the invention".

Compounds of formula (I) can exist in the form of salts, for example acid addition salts or, in certain cases salts of organic and inorganic bases such as carboxylate, sulfonate and phosphate salts. All such salts are within the scope of this invention, and references to compounds of formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as dichloromethane, 1,4-dioxane, ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, acetic, propanoic, butanoic, malonic, glucuronic and lactobionic acids. One particular salt is the hydrochloride salt. Another particular salt is the hydrogensulfate.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

In one embodiment, the compound of formula (I) is (2R,5S)-7-Methyl-2-[4-methyl-6-[4-(trifluoromethyl)-phenyl]pyrimidin-2-yl]-1,7-diazaspiro[4.4]nonan-6-one hydrochloride (E1)

In an alternative embodiment, the compound of formula (I) is (2R,5S)-7-Methyl-2-[4-methyl-6-[4-(trifluoromethyl)-phenyl]pyrimidin-2-yl]-1,7-diazaspiro[4.4]nonan-6-one sulfuric acid salt (E2).

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention. In one embodiment, the pharmaceutically acceptable solvates of the compounds of the invention include the hydrate thereof. In a further embodiment, the compound of formula (I) is (2R,5S)-7-Methyl-2-[4-methyl-6-[4-(trifluoromethyl)-phenyl]pyrimidin-2-yl]-1,7-diazaspiro[4.4]nonan-6-one sulfuric acid salt hydrate (E3).

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Also included within the scope of the compound and various salts of the invention are polymorphs thereof.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

In one embodiment, the invention provides compounds of any one of formulae (Ia)-(Id):

(Ia)
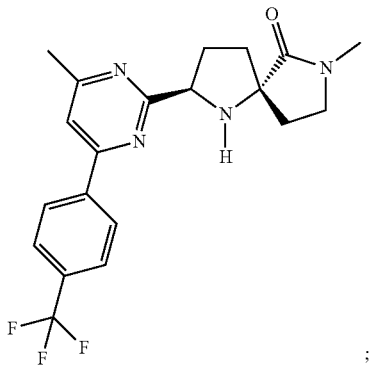

(Ib)
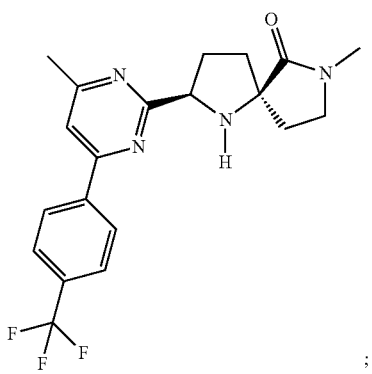

(Ic)
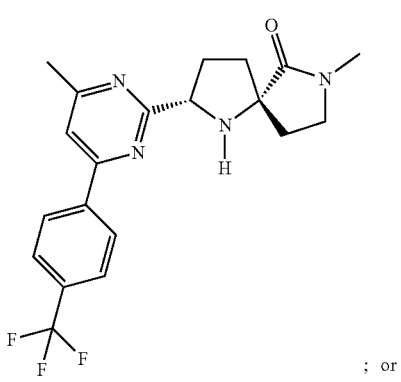

; or (Id)
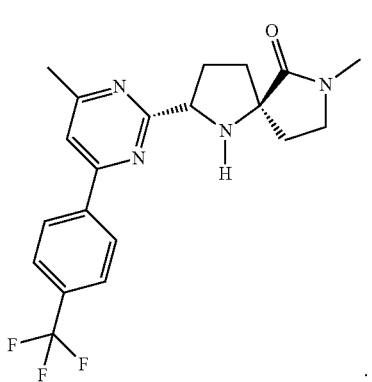

In a further embodiment, the invention provides compounds of formula (Ia). Representative examples of compounds of formula (Ia) include Examples 1-3 described herein.

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

According to a further aspect of the invention there is provided a process for preparing a compound of formula (I) as herein defined which comprises:

(a) forming a compound of formula (I) by performing a ring closure reaction of a compound of formula (II) followed by reduction of the resulting imine (IIA):

(II)
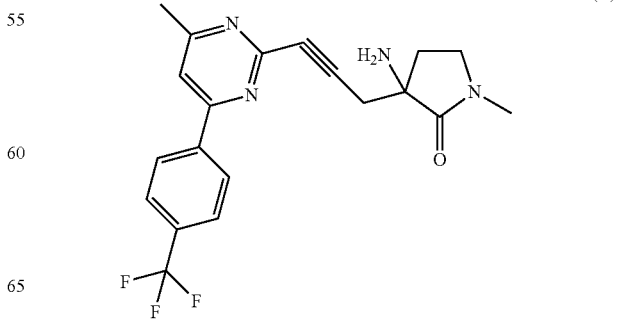

-continued

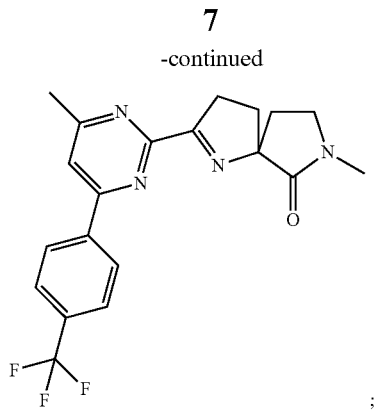
(IIA)

(b) deprotection of a protected derivative of a compound of formula (I);

(c) optional formation of a pharmaceutically acceptable salt of a compound of formula (I).

Process (a) typically comprises treating the compound of formula (II) with a suitable reagent, such as silver trifluoromethanesulfonate (AgOTf), with stirring at a suitable temperature, such as 40° C., for a suitable time period, such as 3 to 7 days, followed by reduction of the resulting imine (IIA) by a hydride reducing agent such as sodium triacetoxyborohydride in a solvent system such as aqueous hydrochloride acid and dichloromethane, or by using borane or a modified borane such as tertiarybutylamine:borane complex, or hydrogenation over a suitable catalyst such as platinum.

Compounds of formula (II) may be prepared in accordance with Scheme 1:

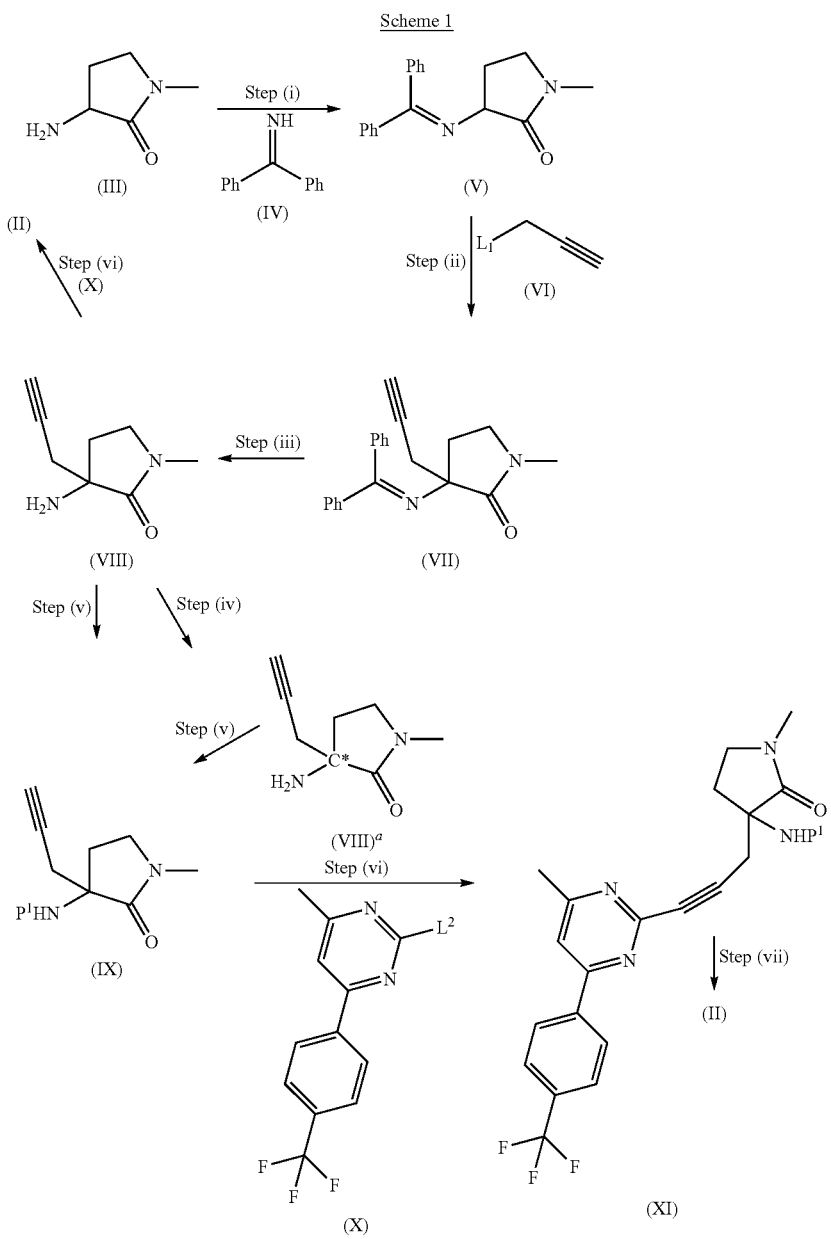

wherein $L^1$ represents a suitable leaving group, such as a halogen atom (i.e. bromine) and $L^2$ represents a suitable leaving group, such as a halogen atom (i.e. iodine) and $P^1$ represents a suitable protecting group, such as Boc.

Step (i) typically comprises reacting a compound of formula (III) with a compound of formula (IV) in the presence of a suitable solvent, such as dichloroethane (DCE).

Step (ii) typically comprises reacting a compound of formula (V) with a compound of formula (VI) in the presence of a suitable base such as potassium tert-butoxide and a suitable solvent, such as tetrahydrofuran (THF).

Step (iii) typically comprises deprotecting a compound of formula (VII) with a suitable acidic reagent, such as citric acid.

Step (iv) comprises a chiral resolution in which one chiral diastereomeric salt form of (VIII) is crystallised and separated from a more soluble epimer, for example by fractional crystallisation of (VIII) with a chiral acid such as mandelic acid or 2-(6-methoxy-2-naphthyl)propanoic acid in a suitable solvent such as THF, acetonitrile or isopropyl alcohol. The chiral form $(VIII)^a$ may be liberated by treating the salt with a base, such as a resin-bound base, in a suitable solvent such as methanol.

Step (v) typically comprises treating a compound of formula (VIII) with a suitable amine protecting reagent, such as $Boc_2O$, in the presence of a suitable solvent, such as dichloromethane (DCM).

Step (vi) typically comprises reacting a terminal alkyne of formula (IX) or (VIII) with a compound of formula (X) in the presence of a suitable reagent, such as copper iodide, a suitable catalyst, such as $PdCl_2(Ph_3P)_2$, a suitable base, such as diethylamine ($Et_2NH$) or diisopropylamine and a suitable solvent, such as tetrahydrofuran, or tertiarybutyl methyl ether.

Step (vii) typically comprises deprotecting a compound of formula (XI) with a suitable acidic reagent, such as trifluoroacetic acid (TFA) in the presence of a suitable solvent, such as dichloromethane (DCM) or alternatively by using sulphuric acid in a solvent such as 1,4-dioxane.

Compounds of formula (X) may be prepared in accordance with Scheme 2:

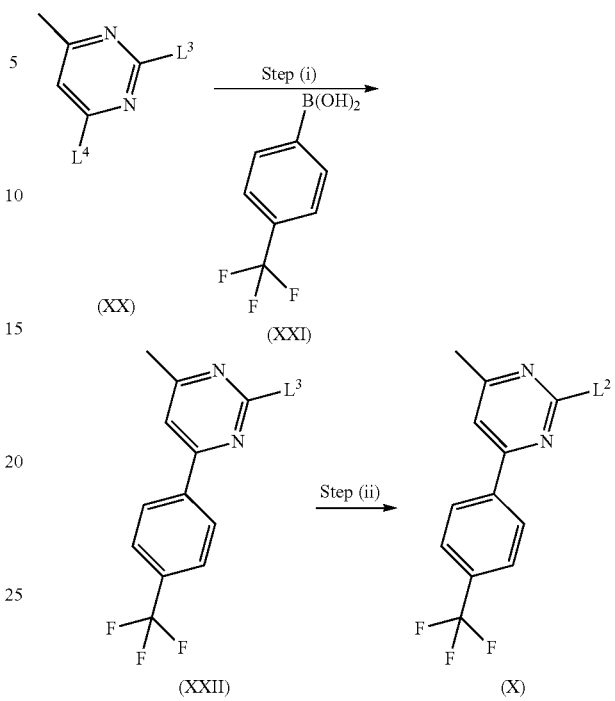

Scheme 2 wherein $L^2$ represents a suitable leaving group, such as a halogen atom (i.e. iodine), $L^3$ represents a suitable leaving group, such as a halogen atom (i.e. chlorine) and $L^4$ represents a suitable leaving group, such as a halogen atom (i.e. chlorine).

Step (i) typically comprises reacting a compound of formula (XX) with a compound of formula (XXI) in the presence of a suitable reagent, such as sodium carbonate, a suitable catalyst, such as $PdCl_2(Ph_3P)_2$, and a suitable solvent, such as dimethoxyethane/water.

When $L^3$ represents chlorine and $L^2$ represents iodine, step (ii) typically comprises reacting a compound of formula (XXI) with hydrogen iodide.

Compounds of formula (IIA) may be prepared in accordance with Scheme 3:

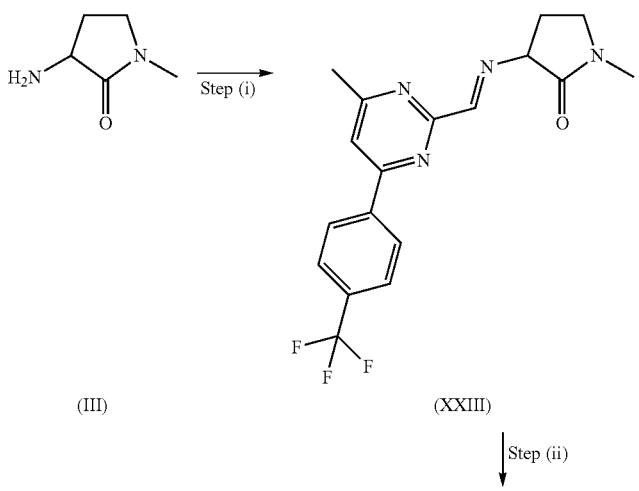

Scheme 3

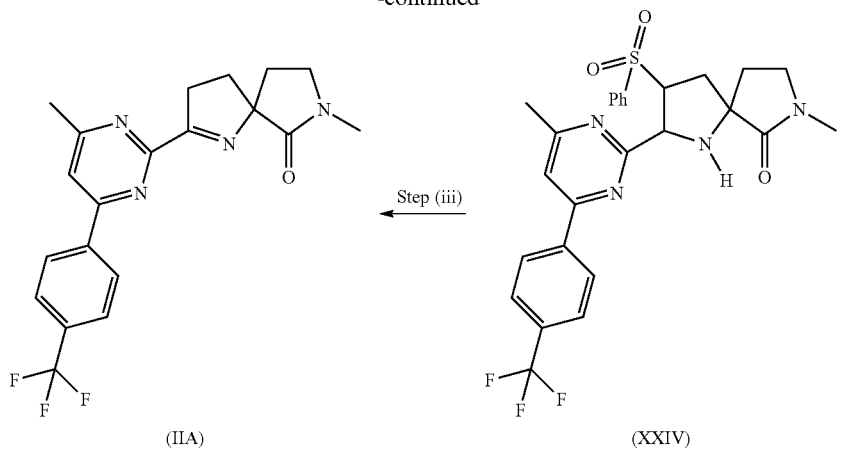

(IIA)  (XXIV)

Step (i) typically comprises condensation of a compound of formula (III) with a carboxyaldehyde compound, including for example a compound of formula (XXVII) (the preparation of which is described below in Scheme 4), in the presence of a dehydrating agent such as magnesium sulfate or molecular sieves in a solvent such as dichloromethane.

Step (ii) typically comprises a [3+2] cycloaddition reaction with phenyl vinyl sulfone catalysed by a transition metal salt such as a silver or copper salt, in the presence of a base and optionally a chiral phosphine ligand.

Step (iii) typically comprises elimination of the phenyl vinyl sulfone typically with a strong base such as potassium tert-butoxide.

The carboxaldehyde compound of formula (XXVII) suitable for reacting with a compound of formula (III) in Scheme 3, may be commercially available but may also be prepared according to Scheme 4:

Scheme 4

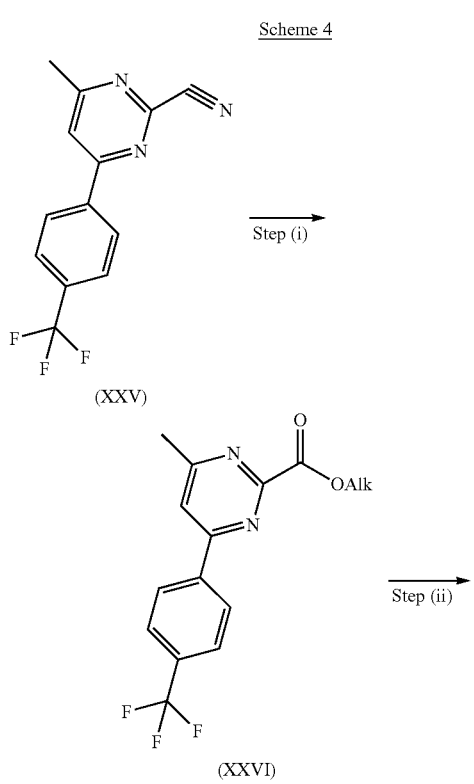

(XXV)

(XXVI)

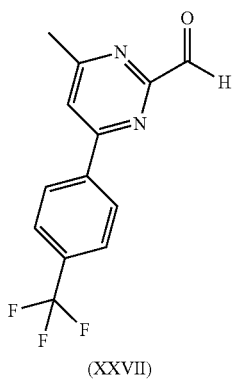

(XXVII)

Step (i) typically comprises an acid catalysed (for example hydrochloride acid) alkoholysis of a 2-cyanopyrimdine with, for example, methanol.

Step (ii) comprises a reduction to an aldehyde using a hindered hydride reducing agent, for example diisobutyl aluminium hydride, in a suitable solvent such as toluene or dichloromethane.

Compounds of formulae (III), (IV), (VI), (XX), (XXI) and (XXV) are either known or may be prepared in accordance with known methodology.

It will be appreciated by those skilled in organic synthesis that two or more chemical steps in the schemes above may be run sequentially without isolation of intermediate materials.

It may also be recognised that isomer separation may occur at any suitable stage in the synthetic sequence. It should be stressed that such chiral separation forms a key aspect of the invention and that such separation may be conducted in accordance with the methodology described herein or may be conducted in accordance with known methodology.

It is also recognised that it may be beneficial to temporarily form a protected derivative of an intermediate in the synthesis, for example, a Boc-protected amine, in order to facilitate chromatographic separation, chiral resolution or to give improved solubility or yields in particular steps.

As discussed hereinabove, it is believed that compounds of the invention may be useful for the treatment of diseases and conditions mediated by modulation of voltage-gated sodium channels.

In one embodiment, the compounds will be state-dependent sodium channel inhibitors.

In another embodiment, the compounds will be subtype NaV1.7 sodium channel state-dependent inhibitors.

In another embodiment, the compounds will be state-dependent sodium channel inhibitors which have a suitable developability profile on oral administration, for example in terms of exposure (Cmax) and/or bioavailability.

In one embodiment, the compounds will be sodium channel inhibitors.

In another embodiment, the compounds will be subtype NaV1.7 sodium channel inhibitors.

In another embodiment, the compounds will be sodium channel inhibitors which have a suitable developability profile on oral administration, for example in terms of exposure (Cmax) and/or bioavailability.

According to a further aspect of the invention, there is provided compounds of the invention for use as a medicament, preferably a human medicament.

According to a further aspect the invention provides the use of compounds of the invention in the manufacture of a medicament for treating or preventing a disease or condition mediated by modulation of voltage-gated sodium channels.

In one particular embodiment, compounds of the invention may be useful as analgesics. For example they may be useful in the treatment of chronic inflammatory pain (e.g. pain associated with rheumatoid arthritis, osteoarthritis, rheumatoid spondylitis, gouty arthritis and juvenile arthritis); musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

Compounds of the invention may be useful in the treatment of neuropathic pain.

Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Compounds of the invention may also be useful in the amelioration of inflammatory disorders, for example in the treatment of skin conditions (e.g. sunburn, burns, eczema, dermatitis, psoriasis); ophthalmic diseases; lung disorders (e.g. asthma, bronchitis, emphysema, allergic rhinitis, non-allergic rhinitis, cough, respiratory distress syndrome, pigeon fancier's disease, farmer's lung, chronic obstructive pulmonary disease, (COPD); gastrointestinal tract disorders (e.g. Crohn's disease, ulcerative colitis, coeliac disease, regional ileitis, irritable bowel syndrome, inflammatory bowel disease, gastroesophageal reflux disease); other conditions with an inflammatory component such as migraine, multiple sclerosis, myocardial ischemia.

In one embodiment, the compounds of the invention are useful in the treatment of neuropathic pain or inflammatory pain as described herein.

Without wishing to be bound by theory, other diseases or conditions that may be mediated by modulation of voltage-gated sodium channels are selected from the list consisting of [the numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10)]:

i) Depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90):

ii) Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

iii) Anxiety disorders including Panic Attack; Panic Disorder including Panic Disorder without Agoraphobia (300.01) and Panic Disorder with Agoraphobia (300.21); Agoraphobia; Agoraphobia Without History of Panic Disorder (300.22), Specific Phobia (300.29, formerly Simple Phobia) including the subtypes Animal Type, Natural Environment Type, Blood-Injection-Injury Type, Situational Type and Other Type), Social Phobia (Social Anxiety Disorder, 300.23), Obsessive-Compulsive Disorder (300.3), Posttraumatic Stress Disorder (309.81), Acute Stress Disorder (308.3), Generalized Anxiety Disorder (300.02), Anxiety Disorder Due to a General Medical Condition (293.84), Substance-Induced Anxiety Disorder, Separation Anxiety Disorder (309.21), Adjustment Disorders with Anxiety (309.24) and Anxiety Disorder Not Otherwise Specified (300.00):

iv) Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic- Persisting Amnestic Disorder, Sedative-, Hypnotic-, or Anxiolytic-Induced Psychotic Disorder, Sedative-, Hypnotic-, or Anxiolytic-lnduced Mood Disorder, Sedative-, Hypnotic-, or Anxiolytic-Induced Anxiety Disorder Sedative-, Hypnotic-, or Anxiolytic-lnduced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide:

v) Enhancement of cognition including the treatment of cognition impairment in other diseases such as schizophrenia, bipolar disorder, depression, other psychiatric disorders and psychotic conditions associated with cognitive impairment, e.g. Alzheimer's disease:

vi) Sleep disorders including primary sleep disorders such as Dyssomnias such as Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47); primary sleep disorders such as Parasomnias such as Nightmare Disorder (307.47), Sleep Terror Disorder (307.46), Sleepwalking Disorder (307.46) and Parasomnia Not Otherwise Specified (307.47); Sleep Disorders Related to Another Mental Disorder such as Insomnia Related to Another Mental Disorder (307.42) and Hypersomnia Related to Another Mental Disorder (307.44); Sleep Disorder Due to a General Medical Condition, in particular sleep disturbances associated with such diseases as neurological disorders, neuropathic pain, restless leg syndrome, heart and lung diseases; and Substance-Induced Sleep Disorder including the subtypes Insomnia Type, Hypersomnia Type, Parasomnia Type and Mixed Type; sleep apnea and jet-lag syndrome:

vi) Eating disorders such as Anorexia Nervosa (307.1) including the subtypes Restricting Type and Binge-Eating/Purging Type; Bulimia Nervosa (307.51) including the subtypes Purging Type and Nonpurging Type; Obesity; Compulsive Eating Disorder; Binge Eating Disorder; and Eating Disorder Not Otherwise Specified (307.50):

vii) Autism Spectrum Disorders including Autistic Disorder (299.00), Asperger's Disorder (299.80), Rett's Disorder (299.80), Childhood Disintegrative Disorder (299.10) and Pervasive Disorder Not Otherwise Specified (299.80, including Atypical Autism).

viii) Attention-Deficit/Hyperactivity Disorder including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9); Hyperkinetic Disorder; Disruptive Behaviour Disorders such as Conduct Disorder including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23):

ix) Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9): and x) Sexual dysfunctions including Sexual Desire Disorders such as Hypoactive Sexual Desire Disorder (302.71), and Sexual Aversion Disorder (302.79); sexual arousal disorders such as Female Sexual Arousal Disorder (302.72) and Male Erectile Disorder (302.72); orgasmic disorders such as Female Orgasmic Disorder (302.73), Male Orgasmic Disorder (302.74) and Premature Ejaculation (302.75); sexual pain disorder such as Dyspareunia (302.76) and Vaginismus (306.51); Sexual Dysfunction Not Otherwise Specified (302.70); paraphilias such as Exhibitionism (302.4), Fetishism (302.81), Frotteurism (302.89), Pedophilia (302.2), Sexual Masochism (302.83), Sexual Sadism (302.84), Transvestic Fetishism (302.3), Voyeurism (302.82) and Paraphilia Not Otherwise Specified (302.9); gender identity disorders such as Gender Identity Disorder in Children (302.6) and Gender Identity Disorder in Adolescents or Adults (302.85); and Sexual Disorder Not Otherwise Specified (302.9).

xi) Impulse control disorder" including: Intermittent Explosive Disorder (312.34), Kleptomania (312.32), Pathological Gambling (312.31), Pyromania (312.33), Trichotillomania (312.39), Impulse-Control Disorders Not Otherwise Specified (312.3), Binge Eating, Compulsive Buying, Compulsive Sexual Behaviour and Compulsive Hoarding.

In another embodiment, diseases or conditions that may be mediated by modulation of voltage gated sodium channels are depression or mood disorders In another embodiment, diseases or conditions that may be mediated by modulation of voltage gated sodium channels are substance related disorders.

In a further embodiment, diseases or conditions that may be mediated by modulation of voltage gated sodium channels are Bipolar Disorders (including Bipolar I Disorder, Bipolar II Disorder (i.e. Recurrent Major Depressive Episodes with Hypomanic Episodes) (296.89), Cyclothymic Disorder (301.13) or Bipolar Disorder Not Otherwise Specified (296.80)).

In a still further embodiment, diseases or conditions that may be mediated by modulation of voltage gated sodium channels are Nicotine-Related Disorders such as Nicotine Dependence (305.1), Nicotine Withdrawal (292.0) or Nicotine-Related Disorder Not Otherwise Specified (292.9).

Compounds of the invention may also be useful in the treatment and/or prevention of disorders treatable and/or preventable with anti-convulsive agents, such as epilepsy including post-traumatic epilepsy, obsessive compulsive disorders (OCD), sleep disorders (including circadian rhythm disorders, insomnia & narcolepsy), tics (e.g. Giles de la Tourette's syndrome), ataxias, muscular rigidity (spasticity), and temporomandibular joint dysfunction.

Compounds of the invention may also be useful in the treatment of bladder hyperrelexia following bladder inflammation.

Compounds of the invention may also be useful in the treatment of neurodegenerative diseases and neurodegeneration such as dementia, particularly degenerative dementia (including senile dementia, Alzheimer's disease, Pick's disease, Huntington's chorea, Parkinson's disease and Creutzfeldt-Jakob disease, motor neuron disease); The compounds may also be useful for the treatment of amyotrophic lateral sclerosis (ALS) and neuroinflamation.

Compounds of the invention may also be useful in neuroprotection and in the treatment of neurodegeneration following stroke, cardiac arrest, pulmonary bypass, traumatic brain injury, spinal cord injury or the like.

Compounds of the invention may also be useful in the treatment of tinnitus, and as local anaesthetics.

The compounds of the invention may also be used in combination with other therapeutic agents. The invention thus provides, in a further aspect, a combination comprising a compound of the invention or a pharmaceutically acceptable derivative thereof together with a further therapeutic agent.

When a compound of the invention or a pharmaceutically acceptable derivative thereof is used in combination with a second therapeutic agent active against the same disease state the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

When used in the treatment or prophylaxis of pain, the compound of formula (I) or a pharmaceutically acceptable salt thereof may be used in combination with other medicaments indicated to be useful in the treatment or prophylaxis of pain of neuropathic origin including neuralgias, neuritis and back pain, and inflammatory pain including osteoarthritis, rheumatoid arthritis, acute inflammatory pain, back pain and migraine. Such therapeutic agents include for example COX-2 (cyclooxygenase-2) inhibitors, such as celecoxib, deracoxib, rofecoxib, valdecoxib, parecoxib, COX-189 or 2-(4-ethoxy-phenyl)-3-(4-methanesulfonyl-phenyl)-pyrazolo[1,5-b]pyridazine (WO 99/012930); 5-lipoxygenase inhibitors; NSAIDs (non-steroidal anti-inflammatory drugs) such as diclofenac, indomethacin, nabumetone or ibuprofen; bisphosphonates, leukotriene receptor antagonists; DMARDs (disease modifying antirheumatic drugs) such as methotrexate; adenosine A1 receptor agonists; sodium channel blockers, such as lamotrigine; NMDA (N-methyl-D-aspartate) receptor modulators, such as glycine receptor antagonists or memantine; ligands for the $\alpha_2\delta$-subunit of voltage gated calcium channels, such as gabapentin, pregabalin and solzira; tricyclic antidepressants such as amitriptyline; neurone stabilising antiepileptic drugs; cholinesterase inhibitors such as galantamine; monoaminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; nicotinic acetyl choline (nACh) receptor modulators; glutamate receptor modulators, for example modulators of the NR2B subtype; $EP_4$ receptor ligands; $EP_2$ receptor ligands; $EP_3$ receptor ligands; $EP_4$ agonists and $EP_2$ agonists; $EP_4$ antagonists; $EP_2$ antagonists and $EP_3$ antagonists; cannabinoid receptor ligands; bradykinin receptor ligands; vanilloid receptor or Transient Receptor Potential (TRP) ligands; and purinergic receptor ligands, including antagonists at $P2X_3$, $P2X_{2/3}$, $P2X_4$, $P2X_7$ or $P2X_{4/7}$; KCNQ/Kv7 channel openers, such as retigabine; additional COX-2 inhibitors are disclosed in U.S. Pat. Nos. 5,474,995, 5,633,272, 5,466,823, 6,310,099 and 6,291,523; and in WO 96/25405, WO 97/38986, WO 98/03484, WO 97/14691, WO 99/12930, WO 00/26216, WO 00/52008, WO 00/38311, WO 01/58881 and WO 02/18374.

The compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The compounds of the invention may be used in combination with antidepressants to treat or prevent depression and mood disorders.

The compounds of the invention may be used in combination with the following agents to treat or prevent bipolar disease: i) mood stabilisers; ii) antipsychotics; and iii) antidepressants.

The compounds of the invention may be used in combination with the following agents to treat or prevent anxiety disorders: i) anxiolytics; and ii) antidepressants.

The compounds of the invention may be used in combination with the following agents to improve nicotine withdrawal and reduce nicotine craving: i) nicotine replacement therapy for example a sublingual formulation of nicotine beta-cyclodextrin and nicotine patches; and ii) bupropion.

The compounds of the invention may be used in combination with the following agents to improve alcohol withdrawal and reduce alcohol craving: i) NMDA receptor antagonists for example acamprosate; ii) GABA receptor agonists for example tetrabamate; and iii) Opioid receptor antagonists for example naltrexone.

The compounds of the invention may be used in combination with the following agents to improve opiate withdrawal and reduce opiate craving: i) opioid mu receptor agonist/opioid kappa receptor antagonist for example buprenorphine; ii) opioid receptor antagonists for example naltrexone; and iii) vasodilatory antihypertensives for example lofexidine.

The compounds of the invention may be used in combination with the following agents to treat or prevent sleeping disorders: i) benzodiazepines for example temazepam, lormetazepam, estazolam and triazolam; ii) non-benzodiazepine hypnotics for example zolpidem, zopiclone, zaleplon and indiplon; iii) barbiturates for example aprobarbital, butabarbital, pentobarbital, secobarbita and phenobarbital; iv) antidepressants; v) other sedative-hypnotics for example chloral hydrate and chlormethiazole.

The compounds of the invention may be used in combination with the following agents to treat anorexia: i) appetite stimulants for example cyproheptidine; ii) antidepressants; iii) antipsychotics; iv) zinc; and v) premenstral agents for example pyridoxine and progesterones.

The compounds of the invention may be used in combination with the following agents to treat or prevent bulimia: i) antidepressants; ii) opioid receptor antagonists; iii) antiemetics for example ondansetron; iv) testosterone receptor antagonists for example flutamide; v) mood stabilisers; vi) zinc; and vii) premenstral agents.

The compounds of the invention may be used in combination with the following agents to treat or prevent autism: i) antipsychotics; ii) antidepressants; iii) anxiolytics; and iv) stimulants for example methylphenidate, amphetamine formulations and pemoline.

The compounds of the invention may be used in combination with the following agents to treat or prevent ADHD: i) stimulants for example methylphenidate, amphetamine formulations and pemoline; and ii) non-stimulants for example norepinephrine reuptake inhibitors (such as atomoxetine), alpha 2 adrenoceptor agonists (such as clonidine), antidepressants, modafinil, and cholinesterase inhibitors (such as galantamine and donezepil).

The compounds of the invention may be used in combination with the following agents to treat personality disorders: i) antipsychotics; ii) antidepressants; iii) mood stabilisers; and iv) anxiolytics.

The compounds of the invention may be used in combination with the following agents to treat or prevent male sexual dysfunction: i) phosphodiesterase V inhibitors, for example vardenafil and sildenafil; ii) dopamine agonists/dopamine transport inhibitors for example apomorphine and buproprion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; v) noradrenaline transport inhibitors for example reboxetine and vii) 5-HT1A agonists, for example flibanserine.

The compounds of the invention may be used in combination with the same agents specified for male sexual dysfunction to treat or prevent female sexual dysfunction, and in addition an estrogen agonist such as estradiol.

Antipsychotic drugs include Typical Antipsychotics (for example chlorpromazine, thioridazine, mesoridazine, fluphenazine, perphenazine, prochlorperazine, trifluoperazine, thiothixine, haloperidol, molindone and loxapine); and Atypical Antipsychotics (for example clozapine, olanzapine, risperidone, quetiapine, aripirazole, ziprasidone and amisulpride).

Antidepressant drugs include serotonin reuptake inhibitors (such as citalopram, escitalopram, fluoxetine, paroxetine and sertraline); dual serotonin/noradrenaline reuptake inhibitors (such as venlafaxine, duloxetine and milnacipran); Noradrenaline reuptake inhibitors (such as reboxetine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

It will be appreciated that references herein to "treatment" extend to prophylaxis, prevention of recurrence and suppression or amelioration of symptoms (whether mild, moderate or severe) as well as the treatment of established conditions.

The compound of the invention may be administered as the raw chemical but the active ingredient is preferably presented as a pharmaceutical formulation.

According to a further aspect, the invention provides a pharmaceutical composition comprising a compound of the invention, in association with one or more pharmaceutically acceptable carrier(s), diluents(s) and/or excipient(s). The carrier, diluent and/or excipient must be "acceptable" in the sense of being compatible with the other ingredients of the composition and not deleterious to the recipient thereof.

The compounds of the invention may be administered in conventional dosage forms prepared by combining a compound of the invention with standard pharmaceutical carriers or diluents according to conventional procedures well known in the art. These procedures may involve mixing, granulating and compressing or dissolving the ingredients as appropriate to the desired preparation.

The pharmaceutical compositions of the invention may be formulated for administration by any route, and include those in a form adapted for oral, topical or parenteral administration to mammals including humans.

The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter-sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, for example from 10-60% by weight, of the active material, depending on the method of administration. Where the compositions comprise dosage units, each unit will for example contain from 5-1000 mg of the active ingredient. The dosage as employed for adult human treatment may range from 10 to 3000 mg per day depending on the route and frequency of administration. For oral administration a typical dose may be in the range of 50 to 1500 mg per day, for example 120 to 1000 mg per day.

It will be recognised by one of skill in the art that the optimal quantity and spacing of individual dosages of a compound of the invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of a compound of the invention given per day for a defined number of days, can be ascertained by those skilled in the art using conventional course of treatment determination tests.

All publications, including, but not limited to, patents and patent applications cited in this specification, are herein incorporated by reference as if each individual publication were specifically and individually indicated to be incorporated by reference herein as though fully set forth.

It will be appreciated that the invention includes the following further aspects. The embodiments described for the first aspect similarly apply to these further aspects. The diseases and conditions described above extend, where appropriate, to these further aspects:

i) A compound of the invention for use in treating or preventing a disease or condition mediated by modulation of voltage-gated sodium channels.

ii) A method of treatment or prevention of a disease or condition mediated by modulation of voltage-gated sodium channels in a mammal comprising administering an effective amount of a compound of the invention.

iii) Use of a compound of the invention in the manufacture of a medicament to treat or prevent a disease or condition mediated by modulation of voltage-gated sodium channels.

iv) Use of a compound of the invention to treat or prevent a disease or condition mediated by modulation of voltage-gated sodium channels.

EXAMPLES

The invention is illustrated by the Examples described below.

In the procedures that follow, after each starting material, reference to a Description or Example by number is typically provided. This is provided merely for assistance to the skilled chemist. The starting material may not necessarily have been prepared from the batch referred to.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

The absolute configuration of the stereocentres within the spiro fused compounds prepared from achiral starting materials and resolved by use of chiral chromatography have been assigned using a combination of optical rotation and NMR spectroscopy (for determining the relative stereochemistry of adjacent stereocentres) and relating these to chiral intermediates and final compounds which have had their absolute configurations determined by single crystal X-ray crystallography. It will be appreciated that some uncertainty exists relating to the absolute configurations referred to herein which have been based primarily on inferred configurations. It will be apparent to the skilled person that absolute configurations can only be definitively characterised by specific analytical determinations, such as X-ray crystallography.

Compounds are named using ACD/Name PRO 6.02 chemical naming software (Advanced Chemistry Development Inc., Toronto, Ontario, M5H2L3, Canada), or using Lexichem's automatic chemical naming software Version 2.0.1 (OpenEye Scientific Software Inc. Santa Fe, N.Mex., USA).

Proton Magnetic Resonance (NMR) spectra are typically recorded on a Bruker instruments at 300, 400 or 500 MHz. Chemical shifts are reported in ppm (δ) using the residual solvent line as internal standard. Splitting patterns are designated as s, singlet; d, doublet; t, triplet; q, quartet; m, multiplet; br, broad. The NMR spectra were recorded at a temperature ranging from 25 to 90° C. When more than one conformer was detected the chemical shifts for the most abundant one is reported.

LC-MS Data (LC-MS) is typically generated on an Waters ZQ Mass Spectrometer, operating in switched ES+ and ES− ionization modes coupled to an Agilent 1100 Series HPLC system with in line Aglient 1100 UV-DAD and Sedere SEDEX 75 ELSD Detection. Instrument control and data acquisition is mediated through the Waters MassLynx—OpenLynx software suite. Separation was performed on a Waters SunFire C18 (30×4.6 mm, 3.5 μm) column Flow Rate: 3.0 mL/min. column temperature 30° C. Injection Volume: 5.0 μL. Mobile phase [A]: 3:97:0.05 (v/v/v) Acetonitrile: Water: Formic Acid. Mobile Phase [B]: 97:3: 0.05 (v/v/v) Acetonitrile: Water: Formic Acid. Gradient: 97% [A] 3% [B] for 0.1 min. Ramp to 3% [A] 97% [B] at 4.0 min. Hold at 97% [B] to 5 min. Return to 97% [A] at 6 min. Detector parameters: UV-DAD: Range 190 to 450 nm, Interval 2 nm, Threshold 0.1 mAU. ELSD: Temperature 40° C., Range 8. Mass Spectrometer: ES+: Mass Range 125 to 625 in 0.50 sec. Interscan delay 0.25 sec. Capillary 4.0 kV. ES−: Mass Range 125 to 625 in 0.50 sec. Interscan delay 0.25 sec. Capillary 3.0 kV.

In the mass spectra only one peak in the molecular ion cluster is usually reported.

Chiral chromatography was typically performed using a ChiralPak™ AD-H or IA column from Daicel® using heptane/ethanol or heptane/ethanol/methanol mixtures as eluent. Analytical chiral HPLC was carried out either on an Agilent 1100 series HPLC system or on a Gilson HPLC system using a 250×4.6 mm column and a flow rate of 1 ml/min. Preparative chiral HPLC was carried out using a Gilson preparative HPLC system on a 250×19 mm semi-preparative column with a flow rate of 18 ml/min.

Flash silica gel chromatography was carried out on silica gel 230-400 mesh (supplied by Merck AG Darmstadt, Germany) or over pre-packed Biotage silica or NH silica cartridges.

Optical rotations were measured using an Optical Activity Ltd AA-10 automatic polarimeter (Cambridge, UK) using a cell of 10 cm path length and in chloroform solution unless otherwise indicated.

SCX cartridges are ion exchange solid phase extraction columns supplied by Varian. The eluent used with SCX cartridges is methanol followed by 0.2-2.0 M ammonia solution in methanol.

In most preparations, purification was performed using Biotage automatic flash chromatography (SP4 or Isolera) systems.

The following abbreviations are used herein:
AD-H ChiralPak AD-H semipreparative column
Boc tertButyloxycarbonyl CHCl₃ Chloroform
DCM Dichloromethane
DCE 1,2-Dichloroethane
DME Dimethoxyethane
EtOAc Ethyl Acetate
Et₂O Ether
HCl Hydrochloric Acid
HPLC High-performance liquid chromatography
IPA Isopropyl alcohol
K₂CO₃ Potassium carbonate
LC-MS Liquid chromatography-Mass spectrometry
MeCN Acetonitrile
MeOMethanol
MgSO₄ Magnesium sulfate
Na₂CO₃ Sodium carbonate
NMR Nuclear Magnetic Resonance
Na₂SO₄ Sodium sulfate
PdCl₂(Ph₃P)₂ Bis(triphenylphosphine)palladium(II) chloride
THF Tetrahydrofuran Preparation of Intermediates Description 1

3-(Benzhydrylidene-amino)-1-methyl-pyrrolidin-2-one (D1)

Method 1: Benzophenone imine [CAS: 1013-88-3] (16.67 g, 91.98 mmol) was added dropwise to a solution of 3-amino-1-methylpyrrolidine-2-one [CAS 119329-48-5] (10 g, 87.60 mmol) in DCE (100 mL) under N₂ and the reaction was heated at reflux for 18 hours. The solvent was evaporated to afford an amber oil. This was purified using flash silica in a large sinter funnel, eluting with 4:1 to 3:7 i-hexane:EtOAc. An incomplete separation was achieved. 3-(Benzhydrylidene-amino)-1-methyl-pyrrolidin-2-one (D1) was isolated (25 g) with approximately 11% of an impurity present, but was used in the next step without further purification;

300 MHz NMR $\delta_H$ (CDCl₃) 2.15-2.49 (2H, m), 2.90 (3H, s), 3.26-3.34 (1H, abq), 3.52 (1H, dt), 4.23 (1H, t), 7.30-7.49 (8H, m), 7.63-7.67 (2H, m).

Method 2: Benzophenone imine (200.04 g, 1103.8 mmol) was added dropwise over 20 minutes to a stirred solution of 3-amino-1-methylpyrrolidine-2-one (120 g, 1051.2 mmol) in DCE (1000 mL) at ambient temp under nitrogen in a 2 L flask fitted with a magnetic stirrer bar. The reagent was washed with further DCE (100 mL). The stirred solution was heated at reflux on a heat-on block at a block temp of 95° C. for 7 h, using a N₂ bubbler with exhaled gas passing through a safety trap then into 2 L of water via an upturned funnel (for scrubbing NH₃ gas, estimated to be approx 23 L). The reaction was left to stand at ambient temp overnight under N₂. The mixture was evaporated to a thick, off-white oil. To this was added Et₂O (700 ml) and to this stirred solution, as it began to crystallize, was added iso-hexane (700 ml) over 2 minutes. The mixture was stirred for 1 h then filtered under suction and washed with Et₂O/iso-hexane (1:1) (500 ml). The white solid was dried at 35° C. under vacuum for 3 h to afford 3-(benzhydrylidene-amino)-1-methyl-pyrrolidin-2-one (D1) (259.4 g, 88.6%). The NMR was consistent with pure material.

Description 2

3-(Benzhydrylidene-amino)-1-methyl-3-prop-2-ynyl-pyrrolidin-2-one (D2)

Method 1: Potassium tert-butoxide 1.7M in THF (32.8 mL, 55.76 mmol) was added dropwise over a period of 80 minutes (by syringe pump) to a solution of the 3-(benzhydrylidene-amino)-1-methyl-pyrrolidin-2-one (14.11 g, 50.692 mmol) (which may be prepared as described in Description 1) and propargyl bromide (6.78 mL, 60.83 mmol) in THF (250 mL) at 0° C. under nitrogen. The reaction was stirred for 2 hours. Additional KO'Bu (5 ml) was added dropwise and stirring was continued for 15 mins. The reaction was quenched by the addition of satd. aq. NaHCO₃ and diluted with EtOAc. The phases were separated, the organic layer was dried (Na₂SO₄) and the solvent evaporated to afford a crude brown oil which solidified on standing. This waxy-solid was suspended in IPA (approx. 30 ml) and stirred for 1 hr. The solid was filtered off, washed with a little IPA to afford 3-(benzhydrylidene-amino)-1-methyl-3-prop-2-ynyl-pyrrolidin-2-one (D2) as a light brown solid (6.26 g);

300 MHz NMR $\delta_H$ (CDCl₃) 1.95 (1H, t), 2.14-2.24 (1H, m), 2.44 (3H, s), 2.45-2.64 (2H, m), 2.94 (2H, t), 3.11 (1H, dt), 7.23-7.48 (8H, m), 7.55-7.59 (2H, m).

Method 2: Potassium tert-butoxide 1.7M in THF (602.08 mL, 1023.5 mmol) was added dropwise over a period of 2.5 h to a stirred solution of 3-(benzhydrylidene-amino)-1-methyl-pyrrolidin-2-one (259 g, 930.48 mmol)) (which may be prepared as described in Description 1) and 80% solution propargyl bromide in toluene (124.37 mL, 1116.6 mmol) in 3A-molecular-sieve-dried reagent grade THF (1900 mL) at −65° C. under nitrogen, in a 5 L flask equipped with an overhead stirrer. After the addition was complete, the mixture was stirred at −65° C. for a further 1 h. The cooling bath was removed and a saturated solution of NaHCO₃ (140 ml) was added over 1 minute (at −60° C.). After a further 5 mins more sat NaHCO₃ solution (1.4 L) was added followed by Et₂O (1.4 L). The mixture was stirred for 1 h then transferred to a separating funnel and water (1.4 L) was added to dissolve all solids. The layers were separated and the aqueous further extracted with Et₂O (2×1 L). The combined organic extracts were re-washed with sat. brine (700 ml), diluted with water (700 ml). The organic layer was dried (MgSO₄) and evaporated to a volume of approx. 500-600 ml whereupon crystallization started to occur. To this stirred mixture was then added iso-hexane (1.6 L). After standing for 15 mins the cream solid was filtered under suction and washed with iso-hexane (500 ml) and dried at 50° C. under vacuum for 5 h. This afforded 3-(benzhydrylidene-amino)-1-methyl-3-prop-2-ynyl-pyrrolidin-2-one (D2) (274 g, 93%). This was pure by NMR but contains some additional water.

Description 3

(3S)-3-Amino-1-methyl-3-prop-2-ynyl-pyrrolidin-2-one (D3S) and (3R)-3-Amino-1-methyl-3-prop-2-ynyl-pyrrolidin-2-one (D3R)

Method 1: Citric acid monohydrate (10.39 g, 49.46 mmol) was added to a solution of 3-(benzhydrylidene-amino)-1- methyl-3-prop-2-ynyl-pyrrolidin-2-one (6.26 g, 19.79 mmol) (which may be prepared as described in Description 2) in THF (150 mL) and the reaction was stirred at room temperature for 18 hours. A colourless solid precipitated out. The solvent was evaporated to give a gummy white solid. This was triturated with Et$_2$O and the solid was washed with further Et$_2$O. The solid was suspended in water/MeOH and purified by SCX (70 g Silca), eluting with water/MeOH, MeOH and finally 0.5M NH$_3$ in MeOH. Fractions containing product were evaporated to afford 3-amino-1-methyl-3-prop-2-ynyl-pyrrolidin-2-one (3.23 g, 21.223 mmol) as a pale yellow oil;

300 MHz NMR $\delta_H$ (CDCl$_3$) 1.65 (2H, br.s), 1.94-2.05 (2H, m), 2.31-2.39 (1H, m), 2.41-2.55 (2H, m), 2.89 (3H, Me), 3.33-3.39 (2H, m).

Method 2: To a stirred solution of 3-(benzhydrylideneamino)-1-methyl-3-prop-2-ynyl-pyrrolidin-2-one (274 g, 865.99 mmol) (which may be prepared as described in Description 2) in a 5L flask equipped with an overhead stirrer, in THF (2.7 L) was added citric acid monohydrate (363.96 g, 1732 mmol) in one portion. The solution was stirred at room temperature for 18 h, giving a thick white precipitate with some sticky solid adhering to the sides of the flask. This sticky solid was loosened with a spatula, then diethyl ether (1.3 L) was added and rapid stirring was continued for a further 1 h. The solid was then filtered under suction and washed efficiently with Et$_2$O (2×1 L) and dried at 50° C. under vacuum for 3 hours. This produced 268g of material. This was recrystallized from hot MeOH (1.9 L); hot solution was filtered under suction to give a clear pale yellow solution. The solution was left to stand for 1 h and Et$_2$O (3 L) was added with stirring. After standing for a further 1 h, the mixture was filtered and washed with MeOH:Et$_2$O (1:2) (1 L) and the solid pressed dry and further dried at 50° C. under vacuum for 6 hours to afford 312 g of the citrate salt, contaminated with methanol. In a separate container, Ambersep 900 (OH) ion exchange resin (2.31 kg) was stirred for 5 minutes with MeOH (2 L) to pre-wash the resin. The suspended resin was filtered under suction and the moist pre-washed resin was added to a stirred suspension of the previously prepared citrate salt in methanol (3 L) in a 10 L vessel equipped with an overhead stirrer. The mixture was stirred for a total of 1.5 h at ambient temp then filtered under suction. The filtered resin was washed with MeOH (2×1.5 L). The filtrate and washings were evaporated in vacuo to an oil which was redissolved in DCM (1.5 L) and dried (Na$_2$SO$_4$), filtered, evaporated to a pale yellow oil, which was dried at RT overnight to give 3-amino-1-methyl-3-prop-2-ynyl-pyrrolidin-2-one (106.9 g, 79.9%). NMR showed this to be pure material identical to that prepared in Description 3, Method 1. A portion of this material (1.75 g, 11.5 mmol) was separated on chiral HPLC using a semi-prep AD-H column, eluting with 20% EtOH/heptane at 18 ml/min. Peaks were identifed at 215 nm:

(3S)-3-amino-1-methyl-3-prop-2-ynyl-pyrrolidin-2-one D3S 549 mg retention time=13.7 mins; Optical rotation α[D/22]=−81.0 (c=0.975, CHCl$_3$).

(3R)-3-amino-1-methyl-3-prop-2-ynyl-pyrrolidin-2-one D3R 407 mg retention time=17.9 mins; Optical rotation α[D/22]=+78.8 (c =0.965, CHCl$_3$).

Method 3: A controlled lab reactor with heater/cooler jacket and an overhead paddle-stirrer was charged with IPA (2250 mL) and (2S)-2-(6-methoxy-2-naphthyl)propanoic acid (84.72 g, 367.92 mmol) was added. The suspension was stirred and warmed to 75° C. giving a solution. A solution of 3-amino-1-methyl-3-prop-2-ynyl-pyrrolidin-2-one (which may be prepared as described in Description 3, Method 2) (55.99 g, 367.92 mmol) in IPA (1100 mL) was then added dropwise over 1.5 hours. In a cooling process, the reaction mixture was stirred at 75° C. for 1 hr then cooled to 55° C. over 1 hr. The reaction was seeded with pure (S) isomer salt at every 1 degree drop in temperature until the seed remained out of solution (ca. 71° C.). The reaction mixture crystallised and was stirred at 55° C. for 1 hr. The mixture was then cooled to 40° C. over approximately 20 minutes and filtered under suction into a pre-warmed filter funnel over a fast filter paper. The vessel was rinsed out with IPA (600 mL) pre-warmed to 40° C. and this was used to wash the collected solids. The solids were dried under suction until no more solvent came out and then were dried in a vacuum oven at 50° C. to give a white solid, 59.37 g (3S)-1-methyl-2-oxo-3-prop-2-ynyl-pyrrolidin-3-yl]ammonium (2S)-2-(6-methoxy-2-naphthyl)propanoate. A portion of this material was removed and dissolved in methanol, passed down an SCX column, washed with methanol and then eluted with 0.5M ammonia in methanol. The ammonia eluent was evaporated to a pale yellow gum, which was analysed by chiral HPLC (20:80 EtOH:heptane, IA column) showing S-isomer 99.5% and R-isomer 0.5%. Ambersep 900-OH (500 g) was stirred in methanol (1000 mL) for 5 minutes, then filtered and dried under suction until no more liquid came out. The washed resin was added to a stirred suspension of S-isomer salt (59.37 g, 155.24 mmol) in methanol (1000 mL). The mixture was stirred for 1 hr, then filtered. The resin was resuspended in methanol (1000 mL) and stirred for an hour and then filtered. The combined filtrates were evaporated to give a slightly cloudy yellow oil. The oil was dissolved in dichloromethane (ca. 200 mL) and dried over magnesium sulphate, filtered and evaporated to give a clear yellow oil (3S)-3-amino-1-methyl-3-prop-2-ynyl-pyrrolidin-2-one (D3S) (22.729 g). This material was characterised as identical to that prepared by chiral chromatography in Method 2.

Method 4: Enriched recrystallisation mother liquors containing, for example, a 91:9 ratio of (3R)-3-amino-1-methyl-3-prop-2-ynyl-pyrrolidin-2-one and its (3S) enantiomer, (27 g) (which may be obtained from the fractional crystalisation procedure described in Description 3 Method 3) were evaporated and dissolved in acetonitrile at 30±5° C. The reaction mass was heated to 70±5° C. and stirred for 10 minutes then slowly cooled to 40±2° C. A seed of the R-amine-(2S)-2-(6-methoxy-2-naphthyl)propanoic acid was introduced and the reaction mixture maintained at 40±2° C. for 1 hr. The reaction mass was cooled to 30±5° C. and filtered. The isolated salt was washed with acetonitrile and dried under vacuum at 47.5±2.5° C. for 6±1 hours to give 18.2 g of the salt with a 99.8% enantiomeric excess of the R isomer. The material was then converted to the free base form as described for the S-enantiomer in Method 3 to give the title compound (D3R). This material was characterised as identical to that prepared by chiral chromatography in Method 2.

Description 4 tert-Butyl N-[(3S)-1-methyl-2-oxo-3-prop-2-ynyl-pyrrolidin-3-yl]carbamate (D4)

Method 1: Boc$_2$O (944.75 mg, 4.33 mmol) was added to a solution of (3S)-3-amino-1-methyl-3-prop-2-ynyl-pyrrolidin-2-one (which may be prepared as described in Description 3) (549 mg, 3.61 mmol) in DCM (20 mL) at 20° C. and the reaction was stirred for 18 hrs. The solvent was evaporated and the residue purified on a Biotage Isolera with a 25g SNAP cartridge, eluting with 0 to 100% EtOAc/i-hexane to afford tert-butyl N-[(3S)-1-methyl-2-oxo-3-prop-2-ynyl-pyrrolidin-3-yl]carbamate (D4) (849 mg, 3.365 mmol, 93.3% yield) as a pale yellow solid.

Method 2: Boc$_2$O (2.77 g, 12.69 mmol) was added to a solution of (3S)-3-amino-1-methyl-3-prop-2-ynyl-pyrrolidin-2-one (which may be prepared as described in Description 3) (1.61 g, 10.58 mmol) in DCM (40 mL) at 20° C. and the reaction was stirred for 18 h. The reaction was warmed to 40° C. and stirred for a further 3 days. The solvent was evaporated and the residue purified using a Biotage Isolera with a 25g SNAP cartridge eluting with 0 to 80% EtOAc/i-hexane to afford tert-butyl N-[(3S)-1-methyl-2-oxo-3-prop-2-ynyl-pyrrolidin-3-yl]carbamate (D4) (2.52 g, 9.9877 mmol, 94.4% yield) as a pale yellow solid;

300 MHz NMR δ$_H$ (CDCl$_3$) 1.45 (9H, s), 2.02 (1H, t), 2.48-2.59 (3H, m), 2.27-2.35 (1H, br.m), 2.92 (3H, s), 2.38-2.44 (2H, m), 5.23 (1H, br.s);

Optical rotation α[D/22]=−2 (c=1.01, CHCl$_3$).

Method 3: To a solution of (3S)-3-amino-1-methyl-3-prop-2-ynyl-pyrrolidin-2-one (which may be prepared as described in Description 3) (72.66 g, 477.4 mmol) in DCM (1000 mL) was added a solution of Boc$_2$O (125.03 g, 572.88 mmol) in DCM (700 mL) in one portion. The reaction was then stirred at 40° C. (bath temp. not internal temp.) over 5 hrs, then at room temperature over the weekend. The reaction was concentrated in vacuo, and the residue was suspended in a mixture of Et$_2$O and isohexane (1:1, 250 mL) and stirred for 30 minutes. The suspension was filtered, and the solid was washed with a mixture of Et$_2$O and isohexane (1:1, 250 mL), followed by isohexane (3×250 mL). The solid was then dried in a vacuum oven for 2 hours (40° C.) to give a white solid, tert-butyl N-[(3S)-1-methyl-2-oxo-3-prop-2-ynyl-pyrrolidin-3-yl]carbamate (D4) (99.25 g);

300 MHz NMR δ$_H$ (CDCl$_3$) 1.43 (9H, s), 2.01 (1H, app.t), 2.45-2.59 (3H, m), 2.78, 2.82 (1H, 2 × br.s), 2.81 (3H, s), 3.35-3.45 (2H, m), 5.23 (1H, br.s).

A second crop was isolated from the filtrate to give a further batch, 5.535 g of similar purity.

Description 5

2-Chloro-4-methyl-6-[4-(trifluoromethyl)phenyl]pyrimidine (D5)

Method 1: To a solution of 2,4-dichloro-6-methyl-pyrimidine (5 g, 30.67 mmol) in 1,2-dimethoxyethane (35 mL) and water (25 mL) was added sodium carbonate (9.75 g, 92.03 mmol), and 4-(trifluoromethyl)-phenylboronic acid (5.53 g, 29.14 mmol). This was degassed with nitrogen for 5 minutes. The bis(triphenylphosphine)palladium (II) dichloride (1.08 g, 1.53 mmol) was then added and the reaction was heated to 90° C. overnight. The solvent was evaporated and the residue was partitioned between water (300 mL) and EtOAc (300 mL). The organics were washed with brine (100 mL), dried over MgSO$_4$ and concentrated in vacuo to afford a yellow oil. The material was purified using a Biotage SP4, 0 to 50% i-hexane/EtOAc and the fractions containing the lower (major) spot were collected and the solvent evaporated to afford the 2-chloro-4-methyl-6-[4-(trifluoromethyl)-phenyl]pyrimidine (D5) (4.65 g, 17.06 mmol, 55.6% yield) as a colourless solid.

300 MHz NMR δ$_H$ (CDCl$_3$) 2.65 (3H, s), 7.57 (1H, s), 7.79 (2H, d), 8.21 (2H, d).

Method 2: To a solution of 4-(trifluoromethyl)phenylboronic acid (116.52 g, 613.5 mmol) in 1,2-dimethoxyethane (1200 mL) was added 2,4-dichloro-6-methylpyrimidine (100 g, 613.5 mmol). To this stirring solution was added a solution of sodium carbonate (195.07 g, 1840.5 mmol) dissolved in water (600 mL) giving some precipitation of the base and then bis(triphenylphosphine)palladium (II) dichloride (2.15 g, 3.07 mmol). The mixture was brought to 50° C. over about 1 hr then stirred at this temperature overnight. The reaction mixture cooled to approx. 30° C., filtered and washed with DCM (approx. 500 mL). The filtrate was evaporated to remove the bulk of the organic solvents. To the residues was added DCM (250 mL) and the phases were separated. The aqueous phase was extracted with DCM (2×250 mL) and the combined extracts were washed with brine (250 mL), dried over magnesium sulphate, filtered and evaporated to a brown gummy solid. The solid was stirred in iso-hexane (150 mL) at 60° C. until the solid had dissolved. The heat was turned off and the flask allowed to cool in the heat-on block naturally. When the solution was at 30° C. seed crystals were added causing immediate crystallisation. The mixture was stood overnight then the crystalline material was crushed and filtered. The solids were washed with cold iso-hexane (2×50 mL) and dried to give the title compound (D5) as a slightly sticky tan solid, (96.17 g) consistent by NMR with that prepared by Method 1.

Description 6

2-Iodo-4-methyl-6-[4-(trifluoromethyl)phenyl]pyrimidine (D6)

Method 1: Hydroiodic acid (57% in water, 9.68 mL, 73.41 mmol) was added portionwise to 2-chloro-4-methyl-6-[4-(trifluoromethyl)phenyl]pyrimidine (which may be prepared as described in Description 5) (1.38 g, 5.06 mmol) in DCM (30 mL) at 20° C. and the dark mixture was stirred for 18 hrs. The mixture was quenched by the addition of sat. aq. K$_2$CO$_3$ (care: gas evolved). After basification, satd. aq. sodium metabisulphite was added and stirring was continued for 5 mins. The mixture was diluted with further DCM and the phases were separated. The organic layer was dried (Na$_2$SO$_4$) and the solvent evaporated to afford 2-iodo-4-methyl-6-[4-(trifluoromethyl)phenyl]pyrimidine (D6) (1.58 g, 4.34 mmol, 85.7% yield) a yellow solid, containing about 20% of the reduced H-compound.

300 MHz NMR δ$_H$ (CDCl$_3$) 2.59 (3H, s), 7.58 (1H, s), 7.77 (2H, d), 8.17 (2H, d)

Method 2: To a solution of 2-chloro-4-methyl-6-[4-(trifluoromethyl)phenyl]pyrimidine (which may be prepared as described in Description 5) (167.5 g, 614.34 mmol) in DCM (1325 mL) was added HI (57% in water) (405.23 mL, 3071.7 mmol) dropwise. The reaction was then stirred at room temperature overnight. Additional DCM (500 mL) was added, and the reaction was filtered. The solid was dried then transferred into a beaker containing water (1 L) and EtOAc (1.25 L). The aqueous was basified to pH 10 with K$_2$CO$_3$, and the layers were stirred until all the solid dissolved. Sodium metabisulfite (8.75 g) was added and the layers were stirred until all solid dissolved. The layers were separated, and the aqueous was re-extracted with EtOAc (200 mL). The combined organics were then dried over MgSO$_4$, filtered and concentrated in vacuo to give the title material (D6) (205.68 g, 564.9 mmol, 92% yield) as a pale orange solid. NMR indicated this was >95% pure.

Description 7 tert-Butyl N-[(3S)-1-methyl-3-[3-[4-methyl-6-[4-(trifluoromethyl)phenyl]pyrimidin-2-yl]prop-2-ynyl]-2-oxo-pyrrolidin-3-yl]carbamate (D7)

Method 1: Copper Iodide (149.46 mg, 0.7800 mmol), followed by PdCl$_2$(Ph$_3$P)$_2$ (275.41 mg, 0.3900 mmol) was added portionwise to a solution of 2-iodo-4-methyl-6-[4-(trifluoromethyl)phenyl]pyrimidine (4 g, 10.99 mmol) (which may be prepared as described in Description 6), tert-butyl N-[(3S)-1-methyl-2-oxo-3-prop-2-ynyl-pyrrolidin-3-yl]carbamate (1.98 g, 7.85 mmol) (which may be prepared as described in Description 4) and Et₂NH (4.06 mL, 39.24 mmol) in THF (50 mL) under N₂ and the reaction was stirred at 20° C. for 18 hrs. The solvent was evaporated and the residue was suspended in EtOAc and washed with water/sat. aq. NaHCO₃. The organics were collected, dried (Na₂SO₄) and the solvent evaporated to afford a brown oil. This was purified using a Biotage SP4, with a 100 g SNAP cartridge, eluting with 50 to 100% EtOAc/i-hexane to afford tert-butyl N-[(3S)-1-methyl-3-[3-[4-methyl-6-[4-(trifluoromethyl)phenyl]pyrimidin-2-yl]prop-2-ynyl]-2-oxo-pyrrolidin-3-yl]carbamate (D7) (4.09 g, 8.3726 mmol) as a pale yellow foam;

300 MHz NMR $\delta_H$ (CDCl₃) 1.46 (9H, s), 2.5-2.75 (2H, m), 2.62 (3H, s), 2.79-2.85 (1H, br.d), 2.98 (3H, s), 3.13-3.19 (1H, br.d), 3.40-3.47 (1H, br.t), 3.63-3.72 (1H, m), 5.35 (1H, br.s), 7.53, 1H, s), 7.78 (2H, d), 8.19 (2H, d).

Method 2: In a 5 L three-necked flask with overhead paddle stirrer and a nitrogen inlet. tert-butyl N-[(3S)-1-methyl-2-oxo-3-prop-2-ynyl-pyrrolidin-3-yl]carbamate (which may be prepared as described in Description 4) (104.79 g, 415.32 mmol) was suspended in tert-Butyl methyl ether (2100 mL). 2-Iodo-4-methyl-6-[4-(trifluoromethyl)phenyl]pyrimidine (which may be prepared as described in Description 6) (166.34 g, 456.85 mmol) was added followed by diisopropylamine (174.63 mL, 1246 mmol) and the mixture was stirred over 20mins. To the suspension was added copper iodide (1.58 g, 8.31 mmol) followed by bis(triphenyl-phosphine)palladium (II) dichloride (2.92 g, 4.15 mmol) and the mixture was stirred at room temperature for 3 hours. Water (1000 mL) was added and the mixture stirred for 30 mins. The phases were separated and the organic phase, washed with water (2×500 mL), dried over magnesium sulphate, filtered and evaporated to a tan foam, 230 g. The material was purified in three batches of approximately 75 g by column chromatography using an 800 g (Biotage 75L) column and eluting with a gradient of acetone in iso-hexane. This gave the title compound (D7) (179.3 g) in good purity by NMR and consistent spectroscopically with that produced by Method 1.

Description 8

(3S)-3-Amino-1-methyl-3-[3-[4-methyl-6-[4-(trifluoromethyl)phenyl]pyrimidin-2-yl]prop-2-ynyl]pyrrolidin-2-one (D8)

Method 1: Trifluoroacetic acid (5 mL, 67.31 mmol) was added to a solution of tert-butyl N-[3S)-1-methyl-3-[3-[4-methyl-6-[4-(trifluoromethyl)phenyl]pyrimidin-2-yl]prop-2-ynyl]-2-oxo-pyrrolidin-3-yl]carbamate (3.83 g, 7.84 mmol) (which may be prepared as described in Description 7) in DCM (50 mL) at 20° C. and the reaction was stirred overnight. The reaction was concentrated and a further portion of trifluoroacetic acid (2 ml) added. Stirring was continued for 3 hrs then solid K₂CO₃ was added (care: gas evolved) and the mixture was diluted with water. The phases were separated and the organic layer was dried (Na₂SO₄). The solvent was evaporated to give (3S)-3-amino-1-methyl-3-[3-[4-methyl-6-[4-(trifluoromethyl)phenyl]pyrimidin-2-yl]prop-2-ynyl]pyrrolidin-2-one (D8) (2.71 g, 6.9775 mmol, 89% yield) as a yellow oil;

300 MHz NMR $\delta_H$ (CDCl₃) 1.95 (2H, br.s), 2.07-2.17 (1H, m), 2.44-2.53 (1H, m), 2.63 (3H, s), 2.72-2.88 (2H, abq), 2.94 (3H, s), 3.38-3.53 (2H, m), 7.53 (1H, s), 7.78 (2H, d), 8.20 (2H, d).

Method 2: To a solution of tert-butyl N-[(3S)-1-methyl-3-[3-[4-methyl-6-[4-(trifluoromethyl)-phenyl]pyrimidin-2-yl]prop-2-ynyl]-2-oxo-pyrrolidin-3-yl]carbamate (which may be prepared as described in Description 7) (99.5 g, 203.68 mmol) in 1,4-dioxane (750 mL) cooled with an ice/water bath to an internal temperature of 15° C. was added conc. sulphuric acid (75 mL, 1407 mmol) dropwise maintaining internal temperature below 20° C. over approximately 35 minutes. After complete addition, the reaction mixture was stirred at room temperature over 30 minutes. The reaction was poured into a beaker and washed in with ethyl acetate (400 mL) and a little water. The mixture was cooled to 15° C. and a solution of sodium carbonate (160 g in 1200 mL water) was added over 5 minutes. The mixture was filtered over a pad of celite and the remaining solids washed with ethyl acetate (400 mL). The filtrate phases were separated and the aqueous phase was extracted with ethyl acetate (2×400 mL). The combined organics were washed with brine (500 mL), dried over magnesium sulphate, filtered and evaporated to yield a foaming amber oil. This was twice dissolved in acetonitrile (100 mL) and evaporated and the resulting yellow foam dried under vacuum to give the title material (D8) in good purity by NMR, consistent spectroscopically with that produced by Method 1.

Description 8a

3-Amino-1-methyl-3-[3-[4-methyl-6-[4-(trifluoromethyl)phenyl]pyrimidin-2-yl]prop-2-ynyl]pyrrolidin-2-one (D8a)

To a stirred solution of 3-amino-1-methyl-3-prop-2-ynyl-pyrrolidin-2-one (which may be prepared as described in Description 3) (2.3 g, 15.11 mmol) in tert-butyl methyl ether (50 mL) was added 2-iodo-4-methyl-6-[4-(trifluoromethyl)-phenyl]pyrimidine (which may be prepared as described in Description 6) (6.05 g, 16.62 mmol). diisopropylamine (6.35 mL, 45.34 mmol) was then added, followed by copper iodide (57.56 mg, 0.300 mmol) and bis(triphenylphosphine)palladium (II) dichloride (106.07 mg, 0.1500 mmol). The reaction was then stirred at room temperature for 5 days. The reaction mixture was transferred to a separating funnel and the flask washed with an additional quantity of tert-butyl methyl ether (15 ml). The organic solution was washed with water (2×50 mL) and brine (50 mL). The organic phase was dried over magnesium sulphate, filtered, and then the magnesium sulphate washed with dichloromethane (30 ml). The filtrate was concentrated at reduced pressure to give a yellow foam. The product was purified by silica gel chromatography eluting with ethyl acetate followed by an increasing percentage of a solution of 10% 0.880 ammonia in methanol, to give the title compound (D8a) as a yellow foam (4.71 g). This racemate was consistent by NMR and mass spectroscopy with the S isomer prepared in Description 8.

Description 9

(5S)-7-Methyl-2-[4-methyl-6-[4-(trifluoromethyl)phenyl]pyrimidin-2-yl]-1,7-diazaspiro[4.4]non-1-en-6-one (D9)

Method 1: Silver trifluoromethanesulphonate (358.56 mg, 1.4 mmol) was added to a solution of (3S)-3-amino-1- methyl-3-[3-[4-methyl-6-[4-(trifluoromethyl)phenyl]pyrimidin-2-yl]prop-2-ynyl]pyrrolidin-2-one (2.71 g, 6.98 mmol) (which may be prepared as described in Description 8) in MeCN (60 mL) at 50° C. and the reaction was stirred for 3 days. Additional AgOTf (10 mol %) was added and stirring was continued for 24 hrs. The solvent was evaporated and the residue was suspended in EtOAc. The organics were washed with water, dried ($Na_2SO_4$) and the solvent evaporated to afford a light brown oil. This was purified using a Biotage Isolera with a 100 g SNAP cartridge, eluting with 0 to 100% (mixture of 1% of 2M $NH_3$ in MeOH; 9% MeOH; 90% EtOAc) in EtOAc, affording the (5S)-7-methyl-2-[4-methyl-6-[4-(trifluoromethyl)phenyl]pyrimidin-2-yl]-1,7-diazaspiro[4.4]non-1-en-6-one (D9) (2.51 g, 6.4626 mmol, 92.6% yield) as a light brown solid;

300 MHz NMR $\delta_H$ (CDCl$_3$) 1.89-2.00 (1H, m), 2.16-2.25 (1H, m), 2.59-2.72 (2H, m), 2.72 (3H, s), 2.92 (3H, s), 3.30-3.45 (2H, m), 3.55-3.78 (2H, m), 7.64 (1H, s), 7.79 (2H,d), 8.26 (2H, d).

Method 2: Silver trifluoromethanesulphonate (9.39 g, 36.56 mmol) was added in a single batch to a solution of (3S)-3-amino-1-methyl-3-[3-[4-methyl-6-[4-(trifluoromethyl)phenyl]-pyrimidin-2-yl]prop-2-ynyl]pyrrolidin-2-one (which may be prepared as described in Description 8) (71 g, 182.81 mmol) in MeCN (1000 mL) and the reaction was heated at 80° C. for 22 hours. The solvent was evaporated and the residue dissolved in DCM (1000 mL). Saturated NaHCO$_3$ (500 ml) and water (500 ml) were added and the mixture shaken. The phases were separated and the organic layer treated with a solution of cysteine (100 g, 825.35 mmol) in water (1500 ml). This mixture was stirred vigorously for 30 minutes. The mixture was filtered through a pad of celite, and the celite washed with DCM (2×100 ml). The phases were separated and the organic layer placed in a large beaker. To this was added a solution of cysteine (50 g, 412.68 mmol) in water (500 ml) and the mixture was stirred for a further 30 minutes. The phases were separated and the organic layer was washed with a mixture of sat. brine (500 ml) and water (500 ml). The organic layer was dried (MgSO$_4$) and the solvent evaporated to afford a dark brown foam. To the foam was added acetone (50 ml) and almost immediately a thick precipitate formed. This was swirled for about 5 minutes prior to slow addition of Et$_2$O (150 ml) over approx. 10 minutes. After addition, the suspension was left to stand for 30 minutes. The solid was filtered off and washed with ether (3×30 ml) to afford the title material as a light brown solid (D9) (49.24 g), pure by NMR and consistent with that produced by Method 1;

Optical Rotation α[D/20]=−141.5 (c=1.12 in CHCl$_3$).

The mother liquors were evaporated to afford a dark foam. This was dissolved in acetone (20 ml) and allowed to stand, with a seeding crystal, for about 15 minutes. Slow crystallization occurred. The mixture was diluted carefully with Et$_2$O (40 ml) and left in a fridge for 18 hours. The supernatant was decanted and the crystalline solid washed with Et$_2$O (3×6 ml) to afford an additional crop of (D9) as a light orange solid (5.31 g) consistent spectroscopically with the earlier batch.

Preparation of Examples

Example 1

(2R,5S)-7-Methyl-2-[4-methyl-6-[4-(trifluoromethyl)-phenyl]pyrimidin-2-yl]-1,7-diazaspiro[4.4] nonan-6-one hydrochloride (E1)

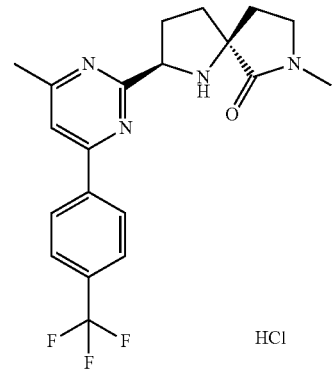

Concentrated aq. HCl (554.67 µL, 6.46 mmol) was added to a solution of the (5S)-8-methyl-3-[4-methyl-6-[4-(trifluoromethyl)phenyl]pyrimidin-2-yl]-4,8-diazaspiro[4.4]non-3-en-9-one (2.51 g, 6.46 mmol) (which may be prepared as described in Description 9) in DCM (60 mL) at 0° C. Finally, Sodium triacetoxyborohydride (4.11 g, 19.39 mmol) was added in a single portion and the resulting mixture was stirred for 90 mins. The reaction was quenched by the addition of sat. aq. Na$_2$CO$_3$ and stirring was continued for 5 mins. The phases were separated, the organic layer was dried (Na$_2$SO$_4$) and the solvent was evaporated to afford an amber oil (2.15 g). This was dissolved in DCE (60 ml) and Boc$_2$O (2.4 g, 11.01 mmol) was added and the reaction was stirred at 50° C. for 18 hrs. The solvent was evaporated to afford a crude brown oil. This was purified using a Biotage SP4 with a100 g SNAP cartridge, eluting with EtOAc (8 CV) to elute the faster Syn isomer A, followed by 0 to 10% MeOH/EtOAc to elute the slower anti isomer B. The syn isomer A: tert-butyl (2S,5S)-7-methyl-2-[4-methyl-6-[4-(trifluoromethyl)phenyl]pyrimidin-2-yl]-6-oxo-1,7-diazaspiro[4.4]-nonane-1-carboxylate (0.6580 g, 1.3414 mmol, 24.4% yield) was obtained as a foam;

m/z 491 (M+H$^+$).

The anti isomer B: tert-butyl (2R,5S)-7-methyl-2-[4-methyl-6-[4-(trifluoromethyl)-phenyl]pyrimidin-2-yl]-6-oxo-1,7-diazaspiro[4.4]nonane-1-carboxylate (1.9 g, 3.8734 mmol, 70.3% yield), was obtained as a foam;

m/z 491 (M+H$^+$),

4M HCl in dioxane (9.68 mL, 38.73 mmol) was added to a solution of the anti isomer B, tert-butyl (2R,5S)-7-methyl-2-[4-methyl-6-[4-(trifluoromethyl)phenyl]pyrimidin-2-yl]-6-oxo-1,7-diazaspiro[4.4]nonane-1-carboxylate (1.9 g, 3.87 mmol) in DCM (20 mL) at 20° C. and the reaction stirred for 18 hrs. The solvent was evaporated and the residue was suspended in EtOAc. This was treated with sat. NaHCO$_3$ and the phases separated. The organic layer was dried (Na$_2$SO$_4$) and the solvent evaporated to afford a light brown oil (1.47 g). This material was dissolved in MeOH and applied to a SCX (10 g) cartridge. The column was eluted with MeOH, followed by 2M NH$_3$ in MeOH to afford the (2R,5S)-7-methyl-2-[4-methyl-6-[4-(trifluoromethyl)phenyl]pyrimidin-2-yl]-1,7-diazaspiro[4.4]nonan-6-one (1.2 g, 3.0738 mmol, 79.4% yield) as a light brown oil;

300 MHz NMR $\delta_H$ (CDCl$_3$) 1.86-1.97 (1H, m), 2.10-2.31 (4H, m), 2.59-2.68 (1H, m), 2.62 (3H, s), 2.92 (3H, s), 3.10 (1H br.s), 3.27-3.43 (2H, m), 4.85 (1H, t), 7.46 (1H, s), 7.77 (2H, d), 8.21 (2H, d).

1M HCl in Et$_2$O (3.07 mL, 3.07 mmol) was added to a solution of the (2R,5S)-7-methyl-2-[4-methyl-6-[4-(trifluoromethyl)phenyl]pyrimidin-2-yl]-1,7-diazaspiro[4.4]nonan-6-one (1.2 g, 3.07 mmol) in DCM (20 mL) at 20° C. and the reaction stirred for 5 mins. The solvent was evaporated and the residue was triturated from Et$_2$O and dried under vacuum at 40° C. to afford the (2R,5S)-7-methyl-2-[4-methyl-6-[4-(trifluoromethyl)phenyl]pyrimidin-2-yl]-1,7-diazaspiro[4.4]nonan-6-one hydrochloride (E1) (1.07 g, 2.7408 mmol, 89.2% yield) as an off white solid with 5 mol % ether present;

300 MHz NMR $\delta_H$ (MeOD) 2.26-2.57 (4H, m), 2.61-1.71 (1H, m), 2.69 (3H, s), 2.87-2.98 (1H, s), 2.98 (3H, s), 3.53-3.59 (2H, m), 5.84 (1H, t), 7.88 (2H, d), 8.02 (1H, s), 8.95 (2H, d); m/z 391 (M+H$^+$); Optical Rotation $\alpha[D/22]$=+12.1 (c =0.995, MeOH).

Example 2

(2R,5S)-7-Methyl-2-[4-methyl-6-[4-(trifluoromethyl)-phenyl]pyrimidin-2-yl]-1,7-diazaspiro[4.4]nonan-6-one sulfuric acid salt (E2)

(5S)-7-Methyl-2-[4-methyl-6-[4-(trifluoromethyl)phenyl]pyrimidin-2-yl]-1,7-diazaspiro[4.4]non-1-en-6-one (which may be prepared as described in Description 9) (78.34 g, 201.7 mmol) was added to a 5 L three necked round bottomed flask containing an overhead stirrer, 500 ml pressure-equalising dropping funnel with a nitrogen inlet and thermometer. To this was added DCM (1000 mL) and the stirred mixture cooled to approx. −70° C. The dropping funnel was charged with a pre-sonicated solution of borane tert-butylamine (19.3 g, 221.87 mmol) in DCM (200 mL). The borane complex was added slowly maintaining the temperature below −70° C. over approx. 30 minutes. After addtion the reaction was stirred at below −70° C. for 90 minutes. The dropping funnel was charged with 6M HCl (400 ml) and this was added dropwise over approx. 15 minutes. The reaction temperature warmed to −50° C. during the addition. After addition was complete the acetone/dry-ice bath was removed and the reaction mixture warmed to room temperature then stirred for a further 30 minutes. In a separate 10 L flask was added sodium carbonate (200 g) and water (1 L). To this flask was added an overhead stirrer. The reaction mixture was carefully added (note: gas evolution) to the sodium carbonate solution and stirring was maintained until gas evolution ceased. The mixture was transferred to a 6 L separating funnel and the phases were separated. The aqueous layer was washed with DCM (2×200 ml) and the combined organics were dried (MgSO$_4$). The solvent was evaporated to afford 7-methyl-2-[4-methyl-6-[4-(trifluoromethyl)-phenyl]pyrimidin-2-yl]-1,7-diazaspiro[4.4]nonan-6-one as an amber oil (77.8 g), a 96:4 ratio of (2R,5S) and (2S,5S) isomers.

A similarly prepared sample was recrystallised from diethyl ether and isohexane to give the free base form of the title material as a colourless solid with a melting point of 66-67° C. Similarly prepared 7-methyl-2-[4-methyl-6-[4-(trifluoromethyl)-phenyl]pyrimidin-2-yl]-1,7-diazaspiro[4.4]nonan-6-one with a diastereomeric excess of approximately 92% (49 g, 125.51 mmol) in MeCN (700 mL) was suction filtered through a shallow pad of Hyflo to give a clear yellow solution. To this rapidly stirred solution at 50° C. was added 7.5M sulphuric acid (17.6 mL, 132 mmol) over 5 seconds to give a solution which quickly crystallized. The mixture was left to stand at ambient temperature for 2 h then filtered and washed with acetonitrile/Et$_2$O (1:1) (200 ml) then Et$_2$O (150 ml) and dried 50° C. to give the title material (E2) in an 82:1 ratio of (2R,5S) and (2S,5S) isomers (50.6 g) assessed by NMR.

300 MHz NMR $\delta_H$ (MeOD) 2.26-2.56 (4H, m), 2.64-2.74 (1H, m), 2.69 (3H, s), 2.88-2.98 (1H, m), 2.98 (3H, s), 3.53-3.59 (2H, m), 5.35 (1H, t), 7.78 (2H, d), 8.02 (1H, s), 8.46 (2H, d); m/z 391 (M+H$^+$).

A similarly prepared sample was recrystallised from acetonitrile to give the title compound as a cream solid with a melting point of 227-228° C.

Example 3

(2R,5S)-7-Methyl-2-[4-methyl-6-[4-(trifluoromethyl)-phenyl]pyrimidin-2-yl]-1,7-diazaspiro[4.4]nonan-6-one sulfuric acid salt hydrate (E3)

(2R,5S)-7-Methyl-2-[4-methyl-6-[4-(trifluoromethyl)-phenyl]pyrimidin-2-yl]-1,7-diazaspiro[4.4]nonan-6-one sufuric acid salt (which may be formed as described in Example 2) (10 mg) was recrystalised by slow cooling in a dewer flask from hot acetone (2 ml), with sufficient added water to cause solubilisation, to form the title compound (E3), the crystalline monohydrate. This was shown to have the (2R,5S)-configuration by single crystal X-ray crystallography.

Biological Assays

The compounds of the invention were tested in a QPatch NaV1.7 assay.

QPatch NaV1.7 Assay

HEK293-hNaV1.7 cells were grown in DMEM-F12+ 10% FBS culture media at 37° C. At a confluency of 50-70% cells were dissociated from culture flasks & triturated to ensure unicellular cell suspension; cell density was measured & adjusted to 2-3×10$^6$ cells/ml. Recordings were obtained using QPatch16x. The external solution was (in mM): NaCl, 128; KCl, 5; MgCl$_2$, 2; CaCl$_2$, 2; Glucose, 30; HEPES, 15; pH 7.3, 305-315 mOsm. Following seal formation and whole-cell access using internal solution (containing in mM: CsF, 135; EGTA/CsOH, 1/5; HEPES 10; NaCl, 10; pH 7.3, 310-320 mOsM), voltage pulse protocols were applied. Initially a steady state inactivation voltage protocol was used to determine the half-maximal voltage for steady state inactivation (V1/2 SSI). Two holding voltages were used to determine test drug inhibition: −90 mV, where most of the channels are in a closed state; and V1/2 SSI, where half of the channels are inactivated. Currents were elicited every 10 seconds by stepping to a membrane potential of 0 mV for 20 ms. Four-point cumulative concentration responses were derived by determining the peak current amplitude at each concentration of test drug over 120 second application. Curves were fitted with the Hill equation yielding pIC50 values at −90 mV and V1/2 SSI holding potentials.

| Example Number | QP Nav1.7 −90 mV pIC50 | QP Nav1.7 SSI vhalf pIC50 |
|---|---|---|
| 1 | 3.9 | 5.7 |

The invention claimed is:
1. A method for treating neuropathic pain, comprising: administering to the patient an effective amount of a compound of formula (I) which is 7-methyl-2-[4-methyl-6-[4-(trifluoromethyl)-phenyl]pyrimidin-2-yl]-1,7-diazaspiro[4.4]nonan-6-one:

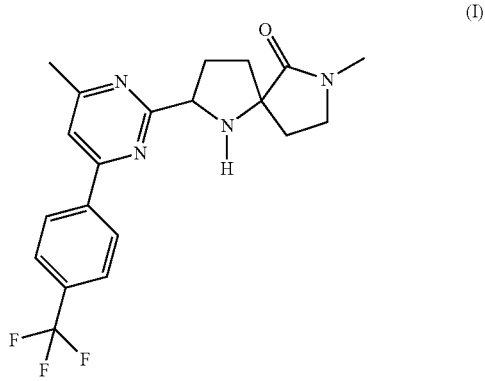 [SMILES: Cc1cc(-c2ccc(C(F)(F)F)cc2)nc(C2CCC3(CCN(C)C3=O)N2)n1]

(I)

or a pharmaceutically acceptable salt or solvate thereof.

2. The method of claim 1, wherein the compound of formula (I) is a compound of formula (Ia):

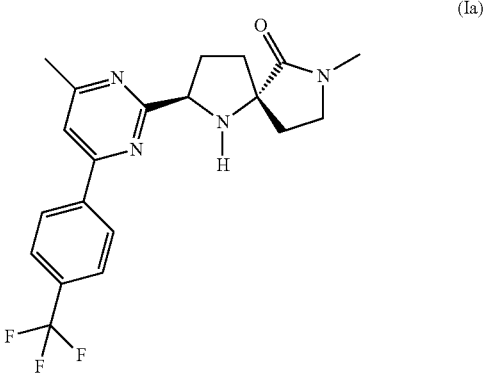 [SMILES: Cc1cc(-c2ccc(C(F)(F)F)cc2)nc([C@H]2CC[C@@]3(CCN(C)C3=O)N2)n1]

(Ia)

or a pharmaceuticaly acceptable salt or solvate thereof.

3. The method of claim 1, wherein the compound of formula (I) or a pharmaceutically acceptable salt or solvate thereof is (2R,5S)-7-Methyl-2-[4-methyl-6-[4-(triflouromethyl)-phenyl]pyrimidin-2-yl]-1,7-diazaspiro[4.4]nonan-6-one hydrochloride (E1).

4. The method of claim 1, wherein the compound of formula (I) or a pharmaceutically acceptable salt or solvate thereof is (2R,5S)-7-Methyl-2-methyl-6-[4-(trifluoromethyl)-phenyl]pyrimidin-2-yl]-1,7-diazaspiro[4.4]nonan-6-one sulfuric acid salt (E2).

5. The method of claim 1, wherein the compound of formula (I) or a pharmaceutically acceptable salt or solvate thereof is (2R,5S)-7-Methyl-2-[4-methyl-6-[4-(trifluorom-ethyl)-phenyl]pyrimidin-2-yl]-1,7-diazaspiro[4.4]nonan-6-one sulfuric acid salt hydrate (E3).

6. The method of claim 2, wherein the compound of formula (Ia) or a pharmaceutically acceptable salt or solvate thereof is (2R,5S)-7-Methyl-2-[4-methyl-6-[4-(triflourom-ethyl)-phenyl]pyrimidin-2-yl]-1,7-diazaspiro[4.4]nonan-6-one hydrochloride (E1).

7. The method of claim 2, wherein the compound of formula (Ia) or a pharmaceutically acceptable salt or solvate thereof is (2R,5S)-7-Methyl-2-[4-methyl-6-[4-(triflourom-ethyl)-phenyl]pyrimidin-2-yl]-1,7-diazaspiro[4.4]nonan-6-one sulfuric acid salt (E2).

8. The method of claim 2, wherein the compound of formula (Ia) or a pharmaceutically acceptable salt or solvate thereof is (2R,5S)-7-Methyl-2-[4-methyl-6-[4(triflourom-ethyl)-phenyl]pyrimidin-2-yl]-1,7-diazaspiro[4.4]nonan-6-one sulfuric acid salt hydrate (E3).

9. A method for treating neuropathic pain, comprising administering to a patient a pharmaceutical composition comprising a compound of formula (I) as defined in claim 1, wherein the compound or a pharmaceutically acceptable salt or solvate thereof is selected from the group consisting of: 7-methyl-2-[4-methyl-6-[4-(trifluoromethyl)-phenyl]pyrimidin-2-yl]-1,7-diazaspiro[4.4]nonan-6-oneor a pharmaceutically acceptable salt or solvate thereof: (2R,5S)-7-Methyl-2-[4-methyl-6-[4-(trifluoromethyl)phenyl]pyrimidin-2-yl]-1,7-diazaspiro[4.4]nonan-6-one hydrochloride (E1);(2R,5S)-7-Methyl-2-[4-methyl-6-[4-(trifluoromethyl)-phenyl]pyrimidin-2-yl]-1,7-diazaspiro[4.4]nonan-6-one sulfuric acid salt (E2); and (2R,5S)-7-Methyl-2-[4-methyl-6-[4-(trifluoromethyl)-phenyl]pyrimidin-2-yl]-1,7-diazaspiro[4.4]nonan-6-one sulfuric acid salt hydrate (E3), and wherein the composition further includes at least one of a pharmaceutically acceptable carrier, diluent and excipient.

10. The method of claim 9, wherein the compound of formula (I) is a compound having the structural formula

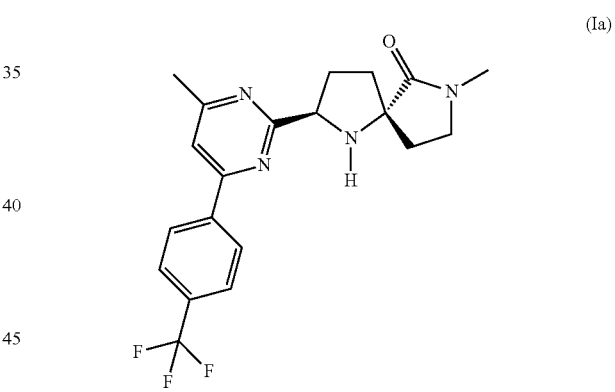

(Ia)

or a pharmaceutically acceptable salt or solvate thereof.

11. The method of claim 10, wherein the compound or a pharmaceutically acceptable salt or solvate thereof is (2R,5S)-7-Methyl-2-[4-methyl-6-[4-(trifluoromethyl)-phenyl]pyrimidin-2-yl]-1,7-diazaspiro[4.4]nonan-6-one hydrochloride (E1).

12. The method of claim 10, wherein the compound or a pharmaceutically acceptable salt or solvate thereof is (2R, 5S)-7-Methyl-2-[4-methyl-6-[4-(trifluoromethyl)-phenyl]pyrimidin-2-yl]-1,7-diazaspiro[4.4]nonan-6-one sulfuric acid salt (E2).

13. The method of claim 10, wherein the compound or a pharmaceutically acceptable salt or solvate thereof is (2R, 5S)-7-Methyl-2-[4-methyl-6-[4-(trifluoromethyl)-phenyl]pyrimidin-2-yl]-1,7-diazaspiro[4.4]nonan-6-one sulfuric acid salt hydrate (E3).

* * * * *

UNITED STATES PATENT AND TRADEMARK OFFICE
CERTIFICATE OF CORRECTION

PATENT NO. : 9,737,536 B2
APPLICATION NO. : 15/163845
DATED : August 22, 2017
INVENTOR(S) : Gerard M. P. Giblin et al.

It is certified that error appears in the above-identified patent and that said Letters Patent is hereby corrected as shown below:

In Claim 2 (at Column 37, Line number 45), the word "pharmaceuticaly" should appear as follows:
--pharmaceutically--

In Claim 4 (at Column 37, Line number 53), the text "(2R,5S)-7-Methyl-2-methyl-6-[4-(trifluoromethyl)-phenyl]pyrimidin-2-yl]-1,7-diazaspiro[4.4]nonan-6-one sulfuric acid salt (E2)" should appear as follows:
--(2R,5S)-7-Methyl-2-[4-methyl-6-[4-(trifluoromethyl)-phenyl]pyrimidin-2-yl]-1,7-diazaspiro[4.4]nonan-6-one sulfuric acid salt (E2)--

In Claim 9 (at Column 38, Line number 17), "7-methyl-2-[4-methyl-6-[4-(trifluoromethyl)-phenyl]pyrimidin-2-yl]-1,7-diazaspiro[4.4]nonan-6-oneor" should appear as follows:
--7-methyl-2-[4-methyl-6-[4-(trifluoromethyl)-phenyl]pyrimidin-2-yl]-1,7-diazaspiro[4.4]nonan-6-one or--

Signed and Sealed this
Twenty-first Day of August, 2018

Andrei Iancu
*Director of the United States Patent and Trademark Office*